United States Patent [19]

Shibano et al.

[11] Patent Number: 5,625,078

[45] Date of Patent: Apr. 29, 1997

[54] PROCESSES FOR THE PRODUCTION OF 13-ETHER DERIVATIVES OF MILBEMYCINS AND NOVEL INTERMEDIATES THEREFOR

[75] Inventors: Mitsugi Shibano, Hiratsuka; Mutsuo Suzuki; Shunshi Kojima, both of Tokyo, all of Japan

[73] Assignee: Sankyo Company, Limited, Tokyo, Japan

[21] Appl. No.: 439,228

[22] Filed: May 11, 1995

Related U.S. Application Data

[62] Division of Ser. No. 114,468, Aug. 31, 1993, Pat. No. 5,461,168.

[30] Foreign Application Priority Data

| Sep. 1, 1992 | [JP] | Japan | 4-233444 |
| Oct. 1, 1992 | [JP] | Japan | 4-263660 |
| Dec. 2, 1992 | [JP] | Japan | 4-322847 |

[51] Int. Cl.$^6$ ................................. C07D 315/00
[52] U.S. Cl. ................................. 549/264
[58] Field of Search ................................. 549/264

[56] References Cited

U.S. PATENT DOCUMENTS

| 4,423,209 | 12/1983 | Mrozik | 549/264 |
| 4,530,921 | 7/1985 | Mrozik | 549/264 |
| 4,696,922 | 9/1987 | Strum et al. | 549/264 |
| 4,831,016 | 5/1989 | Mrozik et al. | 549/264 |
| 4,851,428 | 7/1989 | Asato et al. | 549/264 |
| 4,857,509 | 8/1989 | Frei et al. | 549/264 |
| 4,876,272 | 10/1989 | Asato et al. | 549/264 |
| 4,886,829 | 12/1989 | Asato et al. | 549/264 |
| 4,886,830 | 12/1989 | Asato et al. | 549/264 |
| 4,910,219 | 3/1990 | Sutherland et al. | 549/264 |
| 4,912,090 | 3/1990 | Yanai et al. | 549/264 |
| 4,954,484 | 9/1990 | Gehret | 549/264 |
| 4,959,386 | 9/1990 | Frei et al. | 549/264 |
| 5,030,650 | 7/1991 | Buckwalter et al. | 549/264 |
| 5,126,464 | 6/1992 | Burrows et al. | 549/264 |

FOREIGN PATENT DOCUMENTS

| 0288205 | 10/1988 | European Pat. Off. . |
| 0357460 | 3/1990 | European Pat. Off. . |
| 0444964 | 9/1991 | European Pat. Off. . |
| 0448243 | 9/1991 | European Pat. Off. . |
| 0184173 | 6/1986 | Germany . |

OTHER PUBLICATIONS

B. Frei et al, "Synthesis and Configuration of Some Hydroxymilbemycin Derivatives . . . ", Helvetica Chimica Acta, vol. 73, No. 7, 1990, pp. 1905–1917.
Patent Abstracts of Japan, vol. 17, No. 442, 16 Aug. 1993, of JP-A-05 097 859, 20 Apr. 1993.
Patent Abstracts of Japan, vol. 17, No. 442, 16 Aug. 1993, of JP-A-05 097 860, 20 Apr. 1993.
Patent Abstracts of Japan, vol. 13, No. 494, 8 Nov. 1989, of JP-A-01 197 487, 9 Aug. 1989.
Patent Abstracts of Japan, vol. 11, No. 268, 29 Aug. 1987, of JP-A-62 070 379, 31 Mar. 1987.
Patent Abstracts of Japan, vol. 17, No. 442, 16 Aug. 1993, of JP-A-05 097 863, 20 Apr. 1993.

*Primary Examiner*—Amelia Owens
*Attorney, Agent, or Firm*—Frishauf, Holtz, Goodman, Langer & Chick, P.C.

[57] ABSTRACT

An intermediate useful in the synthesis of milbemycin derivatives having an ether bond at the 13-position and which is represented by the general formula (IIId):

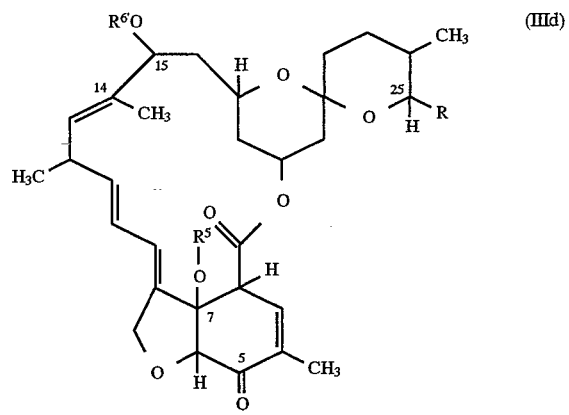

wherein R represents a methyl group, an ethyl group, an isopropyl group or a sec-butyl group, and $R^5$ and $R^6$ each individually represents a hydrogen atom or a protecting group, and related precursors as well as to a process for producing these intermediates.

10 Claims, No Drawings

PROCESSES FOR THE PRODUCTION OF 13-ETHER DERIVATIVES OF MILBEMYCINS AND NOVEL INTERMEDIATES THEREFOR

This is a division of application Ser. No. 08/114,468, filed Aug. 31, 1993, now U.S. Pat. No. 5,461,168.

BACKGROUND TO THE INVENTION

The present invention relates to novel processes for the preparation of 13-ether derivatives of milbemycins, and to novel intermediates for use in such processes.

There are several classes of known compounds with a structure based on a 16-membered macrolide ring, which compounds are obtained by fermentation of various microorganisms or are obtained semi-synthetically by chemical derivatization of such natural fermentation products, and which exhibit acaricidal, insecticidal, anthelmintic and antiparasitic activities. The milbemycins are one such class.

In order to avoid confusion, a standardized system of nomenclature for the milbemycins will be used herein, which follows the normal rules for naming derivatives of organic compounds as recommended by the International Union of Pure and Applied Chemistry, Organic Chemistry Division, Commission on Nomenclature of Organic Chemistry, and which is based primarily on the hypothetical parent compound hereby defined as "milbemycin" and represented by the formula (A):

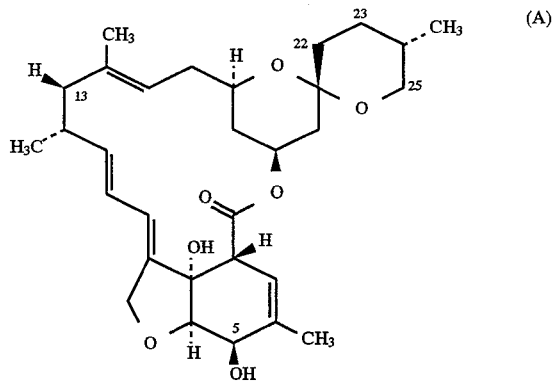

For the avoidance of doubt, formula (A) also shows the numbering of positions of the macrolide ring system applied to those positions most relevant to the compounds of the present invention and of the prior art.

The naturally produced milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the above formula (A) in which there is a hydrogen atom at position 13 and position 25 is substituted with a methyl group, an ethyl group or an isopropyl group, these compounds being designated as milbemycin $A_3$, milbemycin $A_4$ and milbemycin D, respectively.

13-Hydroxy-5-ketomilbemycin derivatives have been disclosed in U.S. Pat. No. 4,423,209, and milbemycin 5-oxime derivatives have been disclosed in U.S. Pat. No. 4,547,520 and in European Patent Publication No. 203 832.

Milbemycins having an ether group at the 13-position have been found to have various useful activities, including particularly strong anthelmintic activity in cattle, for example. The nature of the ether group is not particularly important but it is generally an alkoxy, alkenyloxy, alkynyloxy or aralkoxy group, the substituted phenylalkoxy groups, particularly the phenethoxy group, being most preferred. For example, European Patent Publication No. 357 460 discloses milbemycin derivatives having an optionally substituted phenethoxy group at the 13-position, these compounds having excellent anthelmintic activity.

However, the problem with the 13-ether substituted milbemycins is that there is no commercially viable process for their production. The processes which are described for the production of these compounds in the prior art necessarily employ toxic and/or expensive metal catalysts.

The prior art processes essentially fall into two categories, and the two types of prior art process which are generally used in the manufacture of 13-ether substituted milbemycins involve either:

1) Reacting a milbemycin having a leaving group, such as iodine, in the 13-position with an appropriate alcohol in the presence of a catalyst; or
2) Reacting a 15-hydroxy substituted milbemycin derivative with an appropriate alcohol in the presence of an acid.

In the case of 1) above, a suitable process is described in Japanese Unexamined Patent Publication No. Hei-2-174780, corresponding to European Patent Publication No. 357 460.

In the case of 2) above, a suitable process is described in Japanese Unexamined Patent Publication No. Sho-61-178986, corresponding to U.S. Pat. No. 4,696,945.

With regard to process 1), the catalysts employed are the oxides or salts of silver or mercury. Silver catalysts are very expensive to use in bulk manufacturing operations, even when it is possible to recover the catalyst from the final product. On the other hand, mercury is toxic, and care must be exercised to ensure that all mercury is removed from the final product.

With regard to process 2), there are two main problems. The first problem lies in the reaction of the 15-hydroxy compound with the alcohol. The reaction scheme with partial formulae is as shown below:

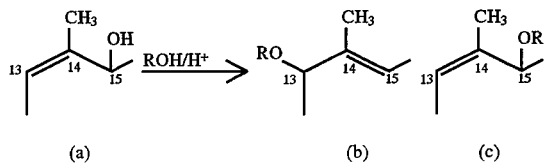

It can be seen that the reaction of the 15-hydroxy compound of partial structure (a) with alcohol yields a mixture of products (b) and (c). In addition, the starting compound must also be protected at the 5-hydroxy position before the reaction can be performed.

The second, more serious problem, with process 2) is concerns the manufacture of the starting material (a). Japanese Unexamined Patent Publication No. Sho. 60-158191, (corresponding to European Patent Publication No. 147852), and Helvetica Chimica Acta, 73, 1905 (1990), describe a process wherein the 15-hydroxy compound (a) can be obtained by treating a 14,15-epoxy compound (d) with a mixture of hydrogen azide and triethylaluminum. The reaction scheme with partial formulae is as follows:

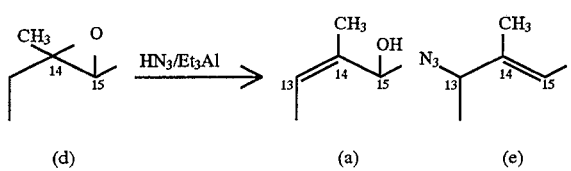

From the above reaction scheme, it can be seen that the compound of formula (a) is obtained together with the 14-azide compound (e). The hydrogen azide used in this process is highly toxic and dangerous (Shin-Jikken Kagaku Kouza, 8, pp. 327 and 328, compiled by Japan Chemical Association, published by Maruzen, Dec. 20, 1976). Triethyl aluminum is also dangerous, because it ignites when brought into contact with water or air, even at room temperature (Shin-Jikken Kagaku Koza, 12, p. 308, compiled by Japan Chemical Association, published by Maruzen, issued on Mar. 20, 1976). Furthermore, as is well known with dry azide compounds (Shin-Jikken Kagaku Koza, 14, p. 1600, compiled by Japan Chemical Association, published by Maruzen, Feb. 20, 1978), there is a danger of the 14-azide compound (e) exploding if exposed to heat or mechanical shock. Thus, the known method for preparing the starting material of formula (a) is not only impractical but also dangerous for bulk manufacturing operations.

Japanese Patent Application No. Hei-3-258036, published in May 1993, discloses a process for preparing 13-substituted milbemycin derivatives starting from a 5-hydroxy milbemycin compound.

BRIEF SUMMARY OF INVENTION

It is an object of the present invention to provide a novel process for the manufacture of 13-substituted milbemycins. It is a further object to provide a process for the manufacture of 13-substituted milbemycins which is safe and cheap to use on a commercial scale. It is a yet further object to provide a method of manufacture of 13-substituted milbemycins which uses a minimal number of reaction steps. It is also an object to provide novel milbemycin derivatives for use in a method of manufacture of 13-substituted milbemycins.

We have now discovered that it is possible to synthesize 13-ether substituted milbemycins from a 5-oxomilbemycin derivative and thereby overcome the above problems.

The invention provides a process for the preparation of a compound of formula (VIIa):

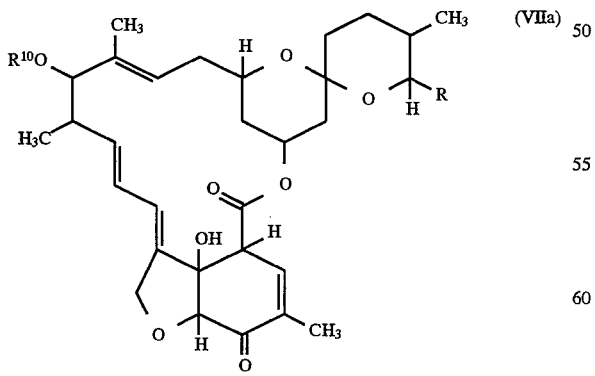

wherein R represents a methyl group, an ethyl group, an isopropyl group or a sec-butyl group, and $R^{10}$ represents an alkyl group having from 1 to 20 carbon atoms; an alkenyl group having from 2 to 6 carbon atoms; an alkynyl group having from 2 to 6 carbon atoms; or an aralkyl group in which the alkyl part has from 1 to 10 carbon atoms and which may be unsubstituted or substituted by 1 or 2 alkoxy groups each having from 1 to 4 carbon atoms, and the aryl part has from 6 to 10 ring carbon atoms and is substituted or unsubstituted, which process comprises the steps:
A. epoxidizing a compound of formula (I):

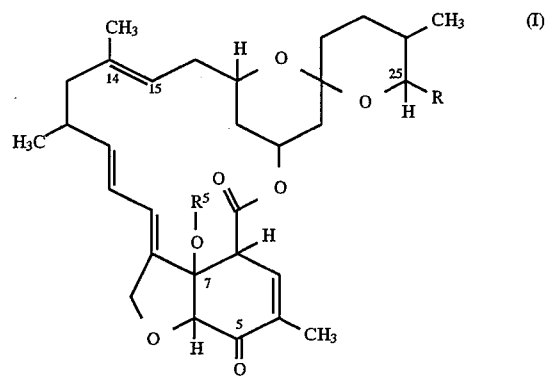

wherein R is as defined above and $R^5$ represents a hydrogen atom or a hydroxy-protected group;
to give a compound of formula (II):

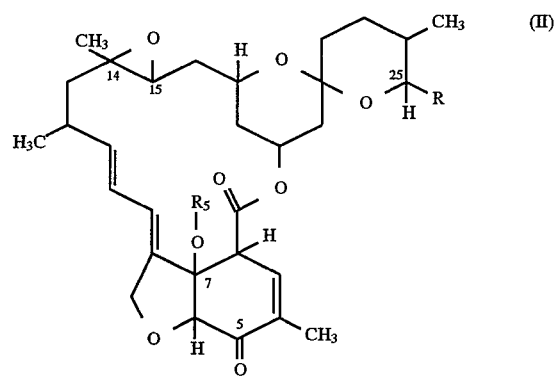

wherein R and $R^5$ are as defined above;
B. subjecting the resulting compound of formula (II) to a ring-opening etherification reaction to give a compound of formula (III):

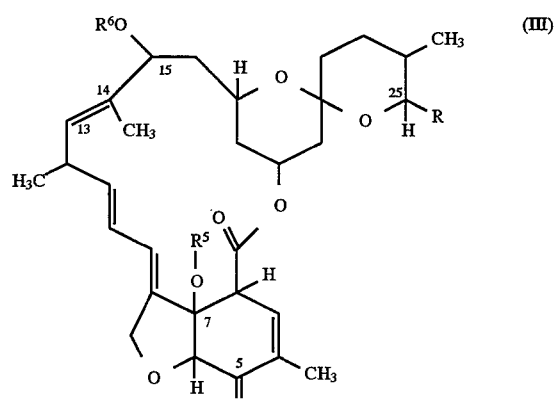

wherein R and $R^5$ are as defined above and $R^6$ represents a hydroxy-protecting group;
and
C. reacting the resulting compound of formula (III) with a compound of formula $R^{10}OH$ to give said compound of formula (VIIa).

Each of the above steps, individually, also forms a part of the invention.

The present invention also provides novel intermediates which can be used in the above process.

DETAILED DESCRIPTION OF INVENTION

Compounds of formula (I) wherein R represents a hydrogen atom are disclosed in Japanese Unexamined Patent Publication No. Hei-1-197487, but use such compounds in the manufacture of 13-substituted milbemycins has not previously been described. In the present invention, the advantage of using such compounds lies in the fact that it is not necessary to protect the 5-hydroxyl group, as in the prior art. Further, as the processes of the prior art first protect the 5-hydroxyl and then eventually result in the production of a 5-oxo group, conventional procedures, such as are described in Japanese Patent Application Sho-62-70379, can be employed in the process of the present invention to hydrogenate the 5-oxo group, thereby restoring the original 5-hydroxy group.

The process of the present invention allows 13-ether milbemycins to be obtained on an industrial scale, in fewer process steps and in higher yields than when compared with conventional reaction processes, without having to employ toxic or dangerous reagents and also without producing potentially dangerous by-products.

The present invention is particularly suitable for the production of milbemycin derivatives having an optionally substituted phenethyl ether bond at the 13-position, and particularly preferred compounds are described in more detail below.

In the general formulae above, the preferred meaning for R is methyl or ethyl, more preferably ethyl.

Step A of the process of the invention epoxidizes a compound of formula (I) to yield a compound of formula (II). If desired, a compound of formula (I) wherein $R^5$ represents a hydrogen atom may first be protected to provide a compound of formula (I) wherein $R^5$ represents a hydroxy-protecting group. The protecting reaction may be effected by any suitable means to prevent subsequent derivatization of the hydroxyl group during epoxidation, and suitable hydroxy-protecting groups represented by $R^5$ include tri-substituted silyl groups.

When $R^5$ represents a tri-substituted silyl group, then suitable groups are those in which all three, or two, or one, of the substituents are alkyl groups having from 1 to 6, preferably from 1 to 4, carbon atoms, and none, one or two of the substituents are unsubstituted or substituted aryl or aralkyl groups, more preferably benzyl, phenyl or substituted phenyl groups, preferably: tri(lower alkyl)silyl groups (such as the trimethylsilyl, triethylsilyl, isopropyldimethylsilyl, t-butyldimethylsilyl, methyldiisopropylsilyl, methyldi-t-butylsilyl and triisopropylsilyl groups); and tri(lower alkyl)silyl groups in which one or two of the alkyl groups have been replaced by aryl or aralkyl groups (such as the diphenylmethylsilyl, diphenylbutylsilyl, diphenyl-t-butylsilyl, diphenylisopropylsilyl, phenyldimethylsilyl, phenyldiisopropylsilyl, dibenzylmethylsilyl, dibenzylbutylsilyl, dibenzyl-t-butylsilyl, dibenzylisopropylsilyl, benzyldimethylsilyl, benzyldiisopropylsilyl and phenethyldimethylsilyl groups).

It is preferred that when $R^5$ represents a hydroxy-protecting group, then it is a group of formula —$SiR^2R^3R^4$, wherein $R^2$, $R^3$ and $R^4$ each independently represents an alkyl group having from 1 to 6, preferably from 1 to 4 carbon atoms.

Suitable alkyl groups having from 1 to 6 carbon atoms include straight or branched chain groups, such as the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the t-butyl and methyl groups, aprticularly methyl groups.

In step A, any suitable epoxidizing agent known in the art can be used to introduce the epoxy group of the compound of formula (II). Conventional epoxidizing agents include those agents which yield peroxide in solution. Examples are given hereinafter, but include the peroxy acids, for example.

The optional protection reaction of step A is generally desirable, as the reagents which are used to epoxidize the 14, 15 position will often also react with the 7-hydroxyl group. For example, when a peroxy acid is employed to introduce the epoxy group, then it is highly preferred to first protect the 7-hydroxyl group, to prevent undesirable side-reactions. However, we have discovered that, if a combination of Oxone (trade mark, potassium peroxymonosulfate) in combination with one or more ketones is used as the epoxidizing agent, then protection is not required, as there is little or no side reaction at the 7-position. In fact, when Oxone/ketones are used, conversion to the desired epoxy compound appears to be substantially stoichiometric.

It will be appreciated that, even when Oxone/ketones are used, the 7-position may be protected, but is not preferred, for the above reasons.

In step B of the process of the invention, the epoxy group of the compound of formula (II) is ring-opened with etherification to give the compound of formula (III), which has a protecting group $R^6$ at the 15-position. Suitable protecting groups are as described above for $R^5$.

In general, it is preferred that $R^6$ represents a group of formula —$SiR^7R^8R^9$, wherein $R^7$, $R^8$ and $R^9$ are each independently selected from the group consisting of alkyl groups having from 1 to 6, preferably 1 to 4 carbon atoms, aryl and aralkyl groups. When one or more of $R^7$, $R^8$ and $R^9$ represents an aryl group, then suitable examples are as defined above, with phenyl being most preferred. When one or more of $R^7$, $R^8$ and $R^9$ represent an aralkyl group, then suitable examples are as defined above, with benzyl being most preferred.

In general, when $R^5$ or $R^6$ represents a tri-substituted silyl group, then the trimethylsilyl group is most preferred.

Subsequent to step B and before step C, the protecting group at the 15-position may be removed to give the 15-hydroxyl milbemycin derivative. This compound may then be used in step C, or may be used to provide further milbemycin derivatives, for example. It will be appreciated that deprotection of the compound of formula (III) is not a preferred step in the process of the invention, as step C can be performed even when the 15-position is protected.

In step C of the process of the invention, the compound of formula (III) undergoes an etherification reaction under conditions which simultaneously deprotect the compound of formula (III) and enable the appropriate alcohol to form an ether group at the 13-position. Suitable conditions are described hereinafter. Subsequent hydrogenation with a mild reducing agent, such as sodium borohydride, restores the 5-hydroxyl group to give the desired end-product.

It will be appreciated that, because the process of the invention is new and starts with a compound not previously described in connection with the preparation of 13-substituted milbemycins, then the intermediates of the process of the invention are also new. Thus, the present invention also provides the intermediates defined above, and as detailed below:

A) Compounds of formula (I):

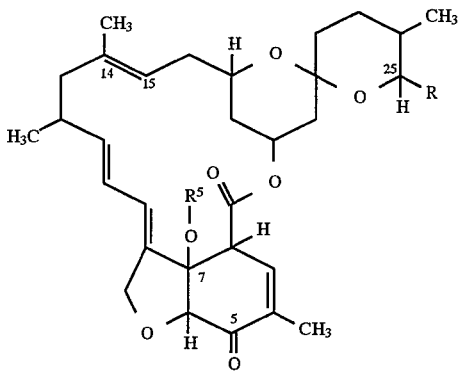

wherein R and $R^5$ are as defined above;

B) Compounds of formula (II):

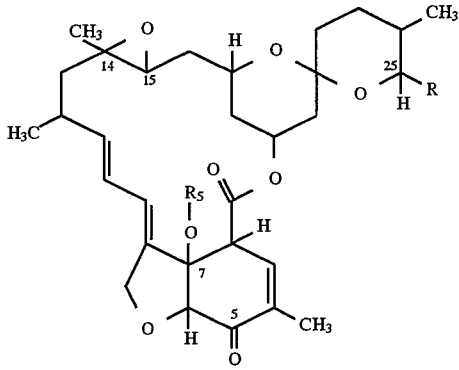

wherein R and $R^5$ are as defined above;

C) Compounds of formula (IIId):

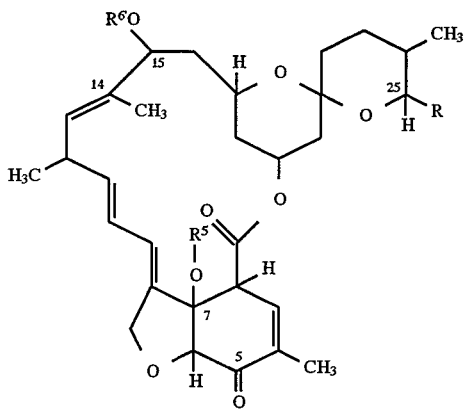

wherein R and $R^5$ are as defined above and $R^{6'}$ represents a hydrogen atom or a protecting group.

In the compounds of formula (VIIa), where $R^{10}$ represents an alkyl group, this may be a straight or branched chain group having from 1 to 20, preferably from 1 to 6, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl, isohexyl, heptyl, octyl, nonyl, decyl, dodecyl, tridecyl, pentadecyl, octadecyl, nonadecyl and icosyl groups, but most preferably the methyl, ethyl and t-butyl groups.

Where $R^{10}$ represents an alkenyl group, this may be a straight or branched chain group having from 2 to 6, preferably 3 or 4, carbon atoms, and examples include the vinyl, allyl, methallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, methallyl, 1-propenyl, isopropenyl and butenyl groups are preferred, the allyl and 2-butenyl groups being most preferred.

Where $R^{10}$ represents an alkynyl group, this may be a straight or branched chain group having from 2 to 6, preferably 3 or 4, carbon atoms, and examples include the ethynyl, propargyl (2-propynyl), 1-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl groups, of which the propynyl and butynyl groups are preferred, the propargyl and 2-butynyl groups being most preferred.

Where $R^{10}$ represents an aralkyl group, the alkyl part preferably has from 1 to 10 carbon atoms and may be unsubstituted or substituted by 1 or 2 alkoxy groups each having from 1 to 4 carbon atoms. The aryl part may have from 6 to 10, preferably 6 or 10, ring carbon atoms and may be unsubstituted or substituted by at least one, preferably from 1 to 5, and more preferably 1 or 2, substituents selected from the group consisting of the groups and atoms defined below for $R^{11}$ and $R^{12}$. Examples of such aralkyl groups include: unsubstituted groups, such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups; and substituted groups, including those substituted on the aryl part with a lower alkyl group, a lower alkoxy group, a nitro group, a halogen atom, a cyano group, or an alkylenedioxy group having from 1 to 3 carbon atoms, preferably a methylenedioxy group, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups.

More preferably, however, the aralkyl group represented by $R^{10}$ is a phenethyl group in which each carbon atom of the alkyl part is substituted by a group or atom $R^{13}$ or $R^{14}$ and the aryl group is substituted by $R^{11}$ and $R^{12}$, all as defined below.

We most prefer that $R^{10}$ represents a 4-N-methanesulfonyl-N-methylamino)phenylethoxy group.

The compounds which can be prepared by the process of the invention are generally as defined above, but the preferred class of compounds is that having the formula (IV):

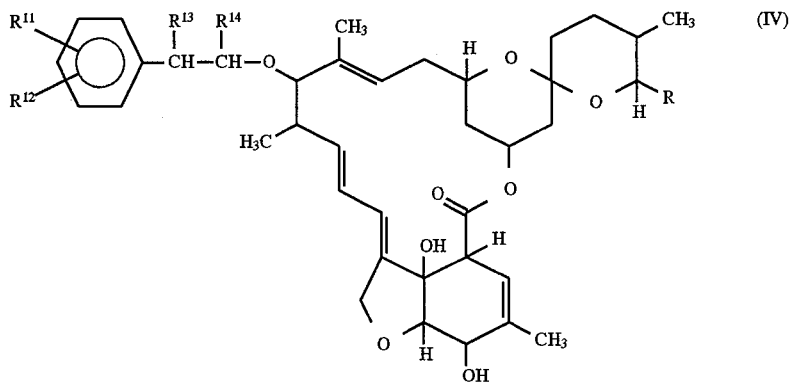

in which:

R is as defined above;

$R^{11}$ and $R^{12}$ are independently selected from the group consisting of: hydrogen atoms; halogen atoms; cyano groups; nitro groups; $C_1$-$C_4$ alkyl groups; substituted $C_1$-$C_4$ alkyl groups having at least one substituent selected from the group consisting of substituents (a), defined below; $C_1$-$C_4$ alkoxy groups; $C_2$-$C_6$ alkoxyalkoxy groups; groups of formula —$(CH_2)_n NHR^{19}$, in which: n represents 0 or the integer 1 or 2, and $R^{19}$ represents a hydrogen atom or a $C_1$-$C_4$ alkyl group;

groups of formula —$(CH_2)_n NR^{19}C(=IO)R^{16}$, in which: n and $R^{19}$ are as defined above, and $R^{16}$ represents: a hydrogen atom; a $C_1$-$C_4$ alkyl group; a substituted $C_1$-$C_4$ alkyl group having at least one substituent selected from the group consisting of substituents (b), defined below; a $C_2$-$C_8$ aliphatic hydrocarbon group having one or two ethylenically unsaturated carbon-carbon double bonds, said group being unsubstituted or having at least one substituent selected from the group consisting of substituents (b), defined below; a $C_2$-$C_8$ alkynyl group; a substituted $C_2$-$C_8$ alkynyl group having at least one substituent selected from the group consisting of substituents (b), defined below; a $C_3$-$C_8$ cycloalkyl group; a substituted $C_3$-$C_8$ cycloalkyl group having at least one substituent selected from the group consisting of substituents (c), defined below; a carbocyclic aryl group having from 6 to 14 ring carbon atoms and being unsubstituted or having at least one substituent selected from the group consisting of substituents (c), defined below; or a heterocyclic group having from 3 to 6 ring atoms of which at least one is a hetero-atom selected from the group consisting of nitrogen, oxygen and sulfur hetero-atoms, said heterocyclic group being monocyclic or fused to one or two benzene rings and being unsubstituted or having at least one substituent selected from the group consisting of substituents (c), defined below;

groups of formula —$(CH_2)_n NR^{19}COCOR^{16}$ in which n, $R^{16}$ and $R^{19}$ are as defined above;

groups of formula —$(CH_2)_n R^{19}COCOOR^{17}$ in which n and $R^{19}$ are as defined above and $R^{17}$ represents a $C_1$-$C_4$ alkyl group, a $_3$-$C_8$ cycloalkyl group or an aralkyl group as defined below;

groups of formula —$(CH_2)_n NR^{19}CHR^{16}NHCOR^{16}$ in which n, $R^{16}$ and $R^{19}$ are as defined above;

groups of formula —$(CH_2)_n NR^{19}CHR^{16}NHCONHR^{16}$ in which n, $R^{16}$ and $R^{19}$ are as defined above;

groups of formula —$(CH_2)_n NR^{19}CHR^{16}NHCOOR^{17}$ in which n, $R^{16}$, $R^{17}$ and $R^{19}$ are as defined above;

groups of formula —$(CH_2)_n NR^{19}C(=Y)YR^{16}$ in which n, $R^{16}$ and $R^{19}$ are as defined above and the two symbols Y are independently selected from the group consisting of oxygen and sulfur atoms;

groups of formula —$(CH_2)_n NR^{19}C(=H)NR^{16'}R^{16'}$ in which n, Y and $R^{19}$ are as defined above, and the two symbols $R^{16'}$ are independently selected from the group consisting of $R^{16}$, or the two, together with the nitrogen atom to which they are attached, form a heterocyclic group having from 3 to 7 ring atoms of which one is said nitrogen atom and 0 or 1 is an additional hetero-atom selected from the group consisting of nitrogen, oxygen and sulfur hetero-atoms;

groups of formula —$(CH_2)_n NR^{19}C(=Y)NR^{16''}NR^{16''}R^{16''}$ in which n, Y and $R^{19}$ are as defined above, and each of the symbols $R^{16''}$ is independently selected from the group consisting of $R^{16}$, or any two of the symbols $R^{16''}$, together with the nitrogen atom to which each is attached, forms a heterocyclic group having from 3 to 7 ring atoms of which one or two is said nitrogen atom or atoms and 0 or 1 is an additional hetero-atom selected from the group consisting of nitrogen, oxygen and sulfur hetero-atoms;

groups of formula —$(CH_2)_n NR^{19}C(=H)NR^{16}NHZ$ in which n, Y, $R^{16}$ and $R^{19}$ are as defined above and Z represents a group of formula —$COOR^{17}$, in which $R^{17}$ is as defined above, a group of formula —$COR^{16}$, in which $R^{16}$ is as defined above, or a group of formula —$SO_2R^{16}$, in which $R^{16}$ is as defined above;

groups of formula —$(CH_2)_n NR^{19}C(=NR^{20})NHR^{20}$ in which n and $R^{19}$ are as defined above and the two symbols $R^{20}$ are independently selected from the group consisting of $R^{16}$, cyano groups, nitro groups, groups of formula —$COOR^{17}$, in which $R^{17}$ is as defined above, and groups of formula —$COR^{16}$, in which $R^{16}$ is as defined above;

groups of formula —$(CH_2)_n NR^{19}C(=NR^{20})R^{16}$ in which n, $R^{16}$, $R^{19}$ and $R^{20}$ are as defined above;

groups of formula —$(CH_2)_n NR^{19}SO_m R^{16}$ in which n, $R^{16}$ and $R^{19}$ are as defined above and m is 1 or 2;

groups of formula —$CONHR^{16}$ in which $R^{16}$ is as defined above; and groups of formula —$COOR^{17}$ in which $R^{17}$ is as defined above;

$R^{13}$ and $R^{14}$ are independently selected from the group consisting of hydrogen atoms, $C_1$-$C_4$ alkyl groups and $C_1$-$C_4$ alkoxy groups; and $R^{15}$ represents a methyl group, an ethyl group, an isopropyl group or a sec-butyl group;

said aralkyl groups have from 1 to 4 carbon atoms in the alkyl part and from 6 to 10 ring atoms in the aryl part, which is a carbocyclic aryl group which is unsubstituted or has at least one substituent selected from the group consisting of substituents (c), defined below;

substituents (a);

halogen atoms, $C_1$-$C_4$ alkoxy groups, $C_1$-$C_4$ alkylthio groups and $C_1$-$C_5$ alkanoyloxy groups;

substituents (b);

$C_3$-$C_8$ cycloalkyl groups; $C_1$-$C_4$ alkoxy groups; $C_1$-$C_4$ alkylthio groups; $C_2$-$C_5$ cyanoalkylthio groups; $C_2$-$C_5$ alkoxycarbonyl groups; halogen atoms; cyano groups; nitro groups, amino groups; carbocyclic aryl groups having from 6 to 10 carbon atoms and being unsubstituted or having at least one substituent selected from the group consisting of substituents (c), defined below; aromatic heterocyclic groups having from 5 to 8 ring atoms of which from 1 to 4 are hetero-atoms selected from the group consisting of nitrogen, oxygen and sulfur hetero-atoms, said heterocyclic group being monocyclic or fused either to a benzene ring or to a heterocyclic group which has 5 or 6 ring atoms of which from 1 to 3 are nitrogen hetero-atoms and being unsubstituted or having at least one substituent selected from the group consisting of substituents (c), defined below; and aryloxy and arylthio groups in which the aryl part has from 6 to 10 carbon atoms and is unsubstituted or has at least one substituent selected from the group consisting of substituents (c), defined below;

substituents (c);

$C_1$-$C_4$ alkyl groups, $C_1$-$C_4$ alkoxy groups, $C_1$-$C_4$ alkylthio groups, $C_1$-$C_5$ alkanoyloxy groups, $C_2$-$C_5$ alkoxycarbonyl groups, halogen atoms, cyano groups, nitro groups, amino groups, mono-and di- alkylamino groups in which the or each alkyl part is $C_1$-$C_4$, carbamoyl groups, mono- and di-alkylcarbamoyl groups in which the or each alkyl part is $C_1$-$C_4$, and $C_1$-$C_5$ alkanoylamino groups;

and salts thereof.

In the compounds of formula (IV), where $R^{11}$ or $R^{12}$ or substituent (a), (b) or (c) represents a halogen atom, this may be a fluorine, chlorine, bromine or iodine atom and is preferably a chlorine or fluorine atom.

Where $R^{11}$, $R^{12}$, $R^{13}$, $R^{14}$, $R^{16}$, $R^{16'}$, $R^{17}$, $R^{19}$ or $R^{20}$ or substituent (c) represents an alkyl group, this has from 1 to 4 carbon atoms and may be a straight or branched chain group. Examples of such groups include the methyl, ethyl, propyl, isopropyl, butyl, sec-butyl and t-butyl groups, of which the methyl, ethyl, propyl, isopropyl, butyl and sec-butyl groups are preferred and the methyl and ethyl groups are most preferred.

Where $R^{11}$, $R^{12}$, $R^{16}$, $R^{16'}$ and $R^{20}$ represents a substituted alkyl group, the alkyl part may be any of the alkyl groups exemplified above and: in the case of $R^{11}$ or $R^{12}$, the substituent is selected from the group consisting of substituents (a); and, in the case of $R^{16}$, $R^{16'}$ or $R^{20}$, the substituent is selected from the group consisting of substituents (b); the substituents being defined above and exemplified elsewhere herein.

Where $R^{11}$, $R^{12}$, $R^{13}$ or $R^{14}$ or substituent (a), (b) or (c) represents an alkoxy group, this has from 1 to 4 carbon atoms and may be a straight or branched chain group. Examples of such groups include the methoxy, ethoxy, propoxy, isopropoxy, butoxy, isobutoxy, sec-butoxy and t-butoxy groups, especially the methoxy, ethoxy, propoxy, isopropoxy and butoxy groups.

Where $R^{11}$ or $R^{12}$ represents a $C_2$-$C_6$ alkoxyalkoxy group, each of the alkoxy parts may have from 1 to 5, preferably from 1 to 4, carbon atoms, provided that the total number of carbon atoms in the two alkoxy groups does not exceed 6, and preferred examples of such alkoxy groups are as given above. Examples of the alkoxyalkoxy groups include the methoxymethoxy, ethoxymethoxy, propoxymethoxy, butoxymethoxy, 1- and 2-methoxyethoxy, 1- and 2-ethoxyethoxy, 1- and 2-butoxyethoxy and 1-, 2- and 3-methoxypropoxy groups, of which the methoxymethoxy, ethoxymethoxy, propoxymethoxy, butoxymethoxy, methoxyethoxy, ethoxyethoxy and butoxyethoxy groups are preferred.

Where $R^{16}$ represents a $C_2$-$C_8$ alkenyl or alkynyl group, it may be, for example, a vinyl, 1-propenyl, allyl, 1-butenyl, 2-butenyl, 3-butenyl, butadienyl, 1-pentenyl, 2-pentenyl, 3-pentenyl, 4-pentenyl, 1,3-dimethylbutenyl, 1-hexenyl, 2-hexenyl, 3-hexenyl, 4-hexenyl, 5-hexenyl, 1,3-, 1,4-, 1,5-, 2,4-, 2,5- and 3,5- hexadienyl, 1-, 2-, 3-, 4-, 5- and 6-heptenyl, 1-, 2-, 3-, 4-, 5-, 6- and 7- octenyl, ethynyl, 1-propynyl, 1-, 2- and 3- butynyl, 1-, 2-, 3-and 4- pentynyl, 1-, 2-, 3-, 4- and 5- hexynyl, 1-, 2-, 3-, 4-, 5- and 6- heptynyl, 1-, 2-, 3-, 4-, 5-, 6- and 7- octynyl and propargyl groups, of which the 1-propenyl, allyl, 1-butenyl, 2-butenyl, 3-butenyl, 1,3-dimethylbutenyl, hexadienyl and propargyl groups are preferred. Such groups may be unsubstituted or they may be substituted by at least one of substituents (b), defined above and exemplified generally herein. However, they are preferably unsubstituted.

Where $R^{16}$, $R^{17}$ or substituent (b) represents a cycloalkyl group, this may contain from 3 to 8 ring atoms, and examples are the cyclopropyl, cyclobutyl, cyclopentyl, cyclohexyl cycloheptyl and cyclooctyl groups, of which the cyclopentyl and cyclohexyl groups are more preferred. Such groups may be unsubstituted or they may be substituted by at least one of substituents (c), defined above and exemplified generally herein. However, they are preferably unsubstituted.

Where $R^{16}$ represents a heterocyclic group, this may be a saturated or unsaturated group containing from 3 to 6 ring atoms, of which at least one, and preferably from 1 to 3, is a nitrogen, oxygen or sulfur atom. More preferably the group has from 0 to 3 such nitrogen atoms, 0, 1 or 2 such oxygen atoms and 0, 1 or 2 such sulfur atoms, provided that the total number of hetero-atoms is not less than 1 and does not exceed 3. Where the group is unsaturated, it may be non-aromatic or aromatic in character. The group may be monocyclic or it may be fused to one or two benzene rings to produce a bicyclic or tricyclic group, in which the heterocyclic part may be aromatic or non-aromatic in character. Examples of such groups include the oxiranyl, oxetanyl, aziridinyl, azetidinyl, thiranyl, thietanyl, furyl, thienyl, pyrrolyl, pyridyl, thiazolyl, isothiazolyl, oxazolyl, isoxazolyl, imidazolyl, pyrazolyl, pyranyl, pyrazinyl, pyridazinyl, pyrimidinyl, benzofuranyl, isobenzofuranyl, benzothienyl, isobenzothienyl, indolyl, quinolyl, isoquinolyl, quinazolinyl, quinoxalinyl, naphthyridynyl, xanthenyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, thiomorpholinyl, iodolinyl, tetrahydroquinolyl, pyrrolidonyl, piperidonyl, pyridonyl, thianthrenyl, chromenyl, phenoxathiinyl, 2H-pyrrolyl, isoindolyl, 3-H-indolyl, indazolyl, phthalazinyl, quinoxalinyl, quinazolinyl, cinnolinyl, carbazolyl, phenanthridinyl, acridinyl, perimidinyl, phenazinylphenothiazinyl, furazanyl, phenoxazinyl, isochromanyl, chromanyl, pyrazolinyl, indolinyl and isoindolinyl groups. Such groups may be unsubstituted or they may have at least one substituent selected from the group consisting of substituents (c), defined above and exemplified elsewhere herein.

Where $R^{11}$ or $R^{12}$ represents a group of formula —$(CH_2)_n NR^{19}C(=Y)NR^{16}R^{16'}$, the two groups represented by $R^{16'}$ may be the same or different and may be selected from those groups represented by $R^{16}$ and defined and exemplified above. Alternatively, the two groups $R^{16'}$, together with the nitrogen atom to which they are attached, may form a nitrogen-containing heterocyclic group, which may optionally have an additional nitrogen, oxygen or sulfur hetero-atom; such a group may contain from 3 to 7 atoms in total (i.e. including the afore-mentioned nitrogen atom) and may be saturated or unsaturated. If it is unsaturated the unsaturation may be aromatic or non-aromatic in character, provided that the group has a nitrogen atom which can provide the nitrogen atom of the group —$NR^{16'}R^{16'}$. Examples of such groups include the aziridinyl, azetidinyl, pyrrolyl, imidazolyl, pyrazolyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, pyrrolidonyl, piperidonyl, pyridonyl, pyrazolinyl, azepinyl, perhydroazepinyl, oxazepinyl and thiazepinyl groups. Such groups may be unsubstituted or they may have at least one substituent selected from the group consisting of substituents (c), defined above and exemplified elsewhere herein.

Where $R^{11}$ or $R^{12}$ represents a group of formula —$(CH_2)_nNR^{19}C(=Y)NR^{16"}NR^{16"}$, $R^{16"}$, the group —$NR^{16"}R^{16"}$ may be a group of formula —$NR^{16}R^{16}$, in which each $R^{16}$ is as defined above, or it may be a group of formula —$NR^{16'}R^{16'}$, which forms a heterocyclic group as exemplified in the preceding paragraph. Alternatively, two of the symbols $R^{16"}$ attached to different nitrogen atoms may form a heterocyclic ring containing at least two nitrogen atoms and optionally another hetero-atom selected from the group consisting of nitrogen, oxygen and sulfur hetero-atoms. Examples of such groups include the divalent groups derived by removal of a hydrogen atom from each of the two adjacent nitrogen atoms of the ring systems: diaziridine, diazete, diazetidine, pyrazolidine, pyrazoline, 1,2-dihydropyridazine, 1,2,3,4-tetrahydropyridazine, 1,2,5,6-tetrahydropyridazine, perhydropyridazine, 1,2-dihydro-1,2-diazepine and perhydro-1,2-diazepine.

Where substituent (a) or (c) represents an alkanoyloxy group, it contains from 1 to 5 carbon atoms and may be a straight or branched chain group. Examples of such groups include the formyloxy, acetoxy, propionyloxy, butyryloxy, isobutyryloxy, valeryloxy, isovaleryloxy and pivaloyloxy groups. Such groups may be substituted or unsubstituted.

Where substituent (a), (b) or (c) is an alkylthio group, this contains from 1 to 4 carbon atoms and may be a straight or branched chain group. Examples of such groups include the methylthio, ethylthio, propylthio, isopropylthio, butylthio, isobutylthio, sec-butylthio and t-butylthio groups.

Where substituent (b) or (c) is an alkoxycarbonyl group, this has a total of from 2 to 5 carbon atoms, i.e. the alkoxy part has from 1 to 4 carbon atoms, and this alkoxy part may be any of those alkoxy groups exemplified above. Examples of such alkoxycarbonyl groups include the methoxycarbonyl, ethoxycarbonyl, propoxycarbonyl, butoxycarbonyl, sec-butoxycarbonyl and t-butoxycarbonyl groups.

Where substituent (b) is a cyanoalkylthio group, this may be a straight or branched chain group having from 2 to 5 carbon atoms in total, i.e. the alkyl part has from 1 to 4 carbon atoms and may be any of those alkyl groups exemplified above. Examples of such cyanoalkylthio groups include the cyanomethylthio, 1-cyanoethylthio, 2-cyanoethylthio, 1-cyanopropylthio, 2-cyanopropylthio, 3-cyanopropylthio, 1-cyanobutylthio, 2-cyanobutylthio, 3-cyanobutylthio, 4-cyanobutylthio, 3-cyano-2-methylpropylthio, 2-cyano-2-methylpropylthio and 2-cyano-1-methylethylthio groups.

Where substituent (b) is an aryl group, this has from 6 to 14 ring carbon atoms and is a carbocyclic group. Examples of such groups include the phenyl, naphthyl (1- or 2-) and anthryl groups, of which the phenyl and naphthyl groups are preferred and the phenyl group is most preferred.

Where substituent (b) is an aromatic heterocyclic group, this has from 5 to 8 ring atoms of which from 1 to 4 are hetero-atoms selected from the group consisting of nitrogen, oxygen and sulfur hetero-atoms and which has at least two conjugated double bonds to give an aromatic character to the ring. More preferably the group has from 0 to 4 such nitrogen atoms, 0, 1 or 2 such oxygen atoms and 0, 1 or 2 such sulfur atoms, provided that the total number of hetero-atoms is not less than 1 and does not exceed 4. The group may be monocyclic or it may be fused to a benzene ring to form a bicyclic ring system. Such groups may be substituted or unsubstituted and, if substituted, have at least one substituent selected from the group consisting of substituents (c), defined above and exemplified elsewhere herein. Examples of such aromatic heterocyclic groups include the pyridyl, thienyl, furyl, pyrrolyl, imidazolyl, triazolyl, tetrazolyl, thiazolyl, oxazolyl, indolyl, benzofuryl, isobenzofuryl, chromenyl, 2H-pyrrolyl, pyrazolyl, isothiazolyl, isoxazolyl, pyrazinyl, pyrimidinyl, pyridazinyl, isoindolyl, 3-H-indolyl, 1H-indazolyl, isoquinolyl, quinolyl, phthalazinyl, quinoxalinyl, quinazolinyl and cinnolinyl groups.

Where substituent (b) is an aryloxy or arylthio group, the aryl part has from 6 to 10 carbon atoms and is a carbocyclic aryl group. Examples include the phenoxy, phenylthio, 1-naphthyloxy, 2-naphthyloxy, 1-naphthylthio and 2-naphthylthio groups, of which the phenoxy and phenylthio groups are preferred. Such groups may be substituted or unsubstituted and, if substituted, the substituent is selected from the group consisting of substituents (c), defined above and exemplified elsewhere herein.

Where substituent (c) is a mono- or di- alkylamino group, the or each alkyl group may have from 1 to 4 carbon atoms and may be a straight or branched chain group. Examples of alkyl groups are given above. Examples of such mono- and di- alkylamino groups include the methylamino, ethylamino, propylamino, isopropylamino, butylamino, dimethylamino, diethylamino, N-methyl-N-ethylamino, N-methyl-N-propylamino and N-ethyl-N-butylamino groups.

Where substituent (c) is a mono- or di- alkylcarbamoyl group, the or each alkyl group may have from 1 to 4 carbon atoms and may be a straight or branched chain group. Examples of alkyl groups are given above. Examples of such mono- and di- alkylcarbamoyl groups include the methylcarbamoyl, ethylcarbamoyl, propylcarbamoyl, isopropylcarbamoyl, butylcarbamoyl, dimethylcarbamoyl, diethylcarbamoyl, N-methyl-N-ethylcarbamoyl, N-methyl-N-propylcarbamoyl and N-ethyl-N-butylcarbamoyl groups.

Where substituent (c) is a $C_1$–$C_5$ alkanoylamino group, the alkanoyl part may be a straight or branched chain group and examples include the formylamino, acetylamino, propionylamino, butyrylamino, isobutyrylamino, valerylamino, isovalerylamino and pivaloylamino groups.

Where $R^{17}$ represents an aralkyl group, the alkyl part has from 1 to 4 carbon atoms and may be any of the alkyl groups exemplified above. The aryl part has from 6 to 10 carbon atoms in its ring and again, may be any of the aryl groups exemplified above. Examples of such aralkyl groups include the benzyl, phenethyl, α-methylbenzyl, 1-phenylpropyl, 2-phenylpropyl, 3-phenylpropyl and 4-phenylbutyl groups, of which the benzyl and phenethyl groups are preferred.

In general, in the discussion above, where reference is made to a substituted group, there is no particular restriction on the number of substituents, except such as may be imposed by the number of substitutable positions, or possibly by steric constraints, each of which is well recognized by those skilled in the art. However, as a general rule, we normally find it convenient to have no more than 3 such substituents, and sometimes fewer, i.e. 1, 2 or 3. More preferably, the number of the substituents is 1, 2 or 3 where the substituent is a halogen atom, and 1 in other cases.

It will also be appreciated that the compounds of formula (IV) may be further derivatized at the 5-position, for example, to provide an ester or salt thereof. The 15-hydroxyl group may also be converted to a hydroxyimino group, if desired.

In the processes of the invention, the most preferred end-products are derivatives of milbemycins $A_4$ and $A_3$, the most preferred compounds being 13-{2-[4-(N-methanesulfonyl-N-methylamino)phenyl]-ethoxy}milbemycin $A_4$ and 13-{2-[4-(N-methanesulfonyl-N-methylamino)phenyl]-ethoxy}milbemycin $A_3$.

In practice, it will often be the case that the compound of formula (I) used as the starting material will comprise a mixture of $A_4$ and $A_3$ milbemycin derivatives (wherein R is a methyl or ethyl group).

The following two reaction schemes, A and B, show two processes of the present invention for obtaining a compound of formula (IV) from a compound of formula (I) wherein $R^5$ represents a hydrogen atom. In the following reaction scheme A, the hydroxy group at position 7 is protected prior to 14, 15-epoxidization. In reaction scheme B, 14, 15-epoxidization is carried out without first protecting the hydroxy group at the 7 position.

It will be appreciated that reaction scheme A involves the compounds of formulae (I), (II) and (III) of the present invention, while reaction scheme B proceeds from a compound of formula (I) wherein $R^5$ represents a hydrogen atom directly to a compound of formula (IIb), without the necessity of first protecting the 7-hydroxyl group.

REACTION SCHEME A

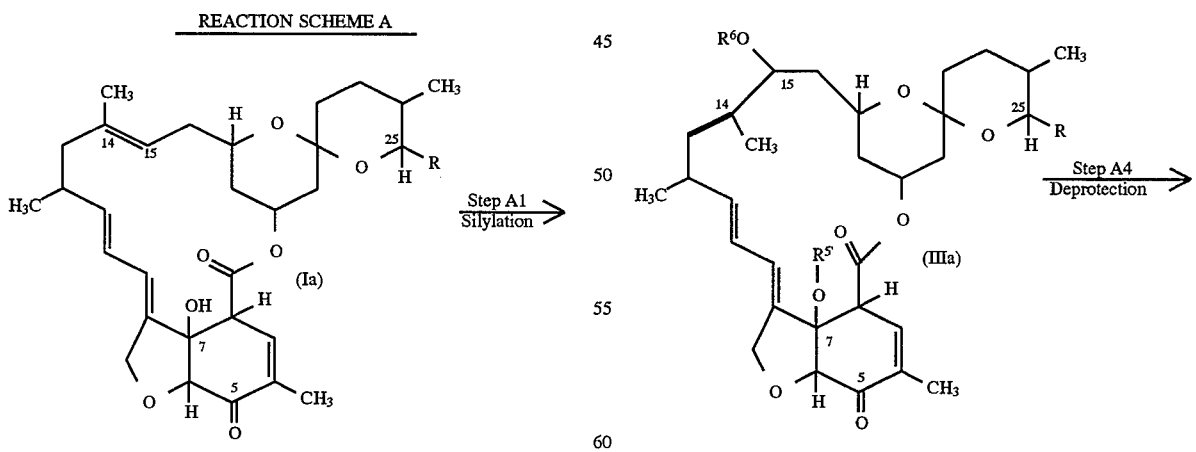
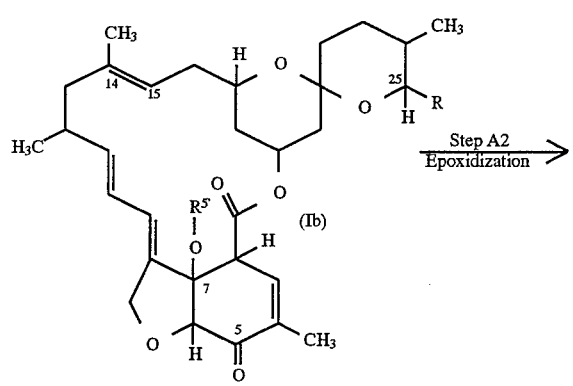
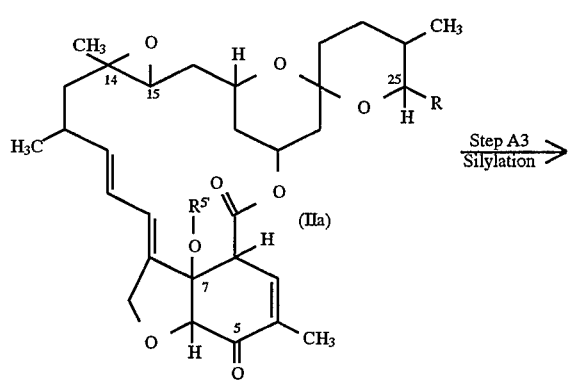

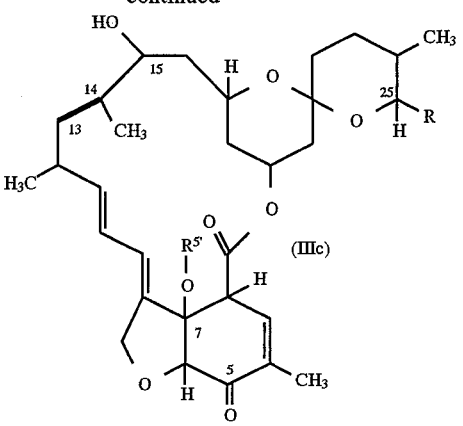

(IIIc)

REACTION SCHEME B

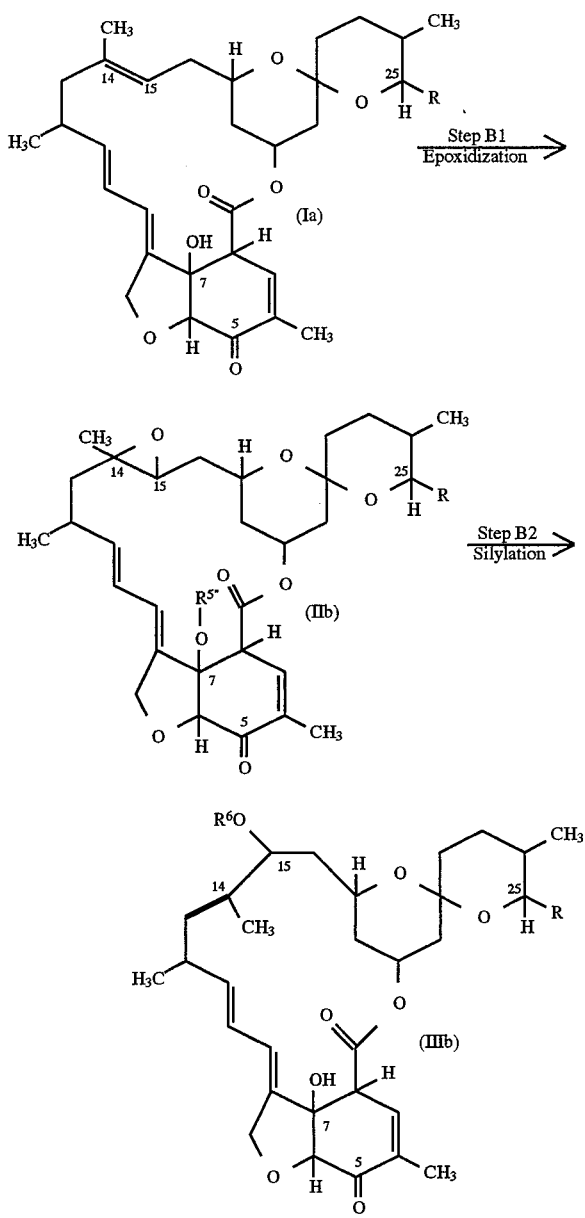

In the above formulas, R and $R^6$ are as defined above, $R^{5'}$ represents a hydroxy-protecting group and $R^{5''}$ represents a hydrogen atom.

Reaction Scheme A

In step A1, a compound of general formula (Ib) is prepared by reacting, in solution, a compound of formula (Ia) with a silylating reagent in the presence of an acid binding agent.

Any acid binding agents suitable for use in the silylation reaction, as are well known in the art, may be employed in step A1, without any particular restrictions. Acid binding agents frequently used for silylation include imidazole, 4-dimethylaminopyridine and triethylamine, any of which may be employed in step A1. We prefer that the acid binding agent is an organic base, such as imidazole or triethylamine, and we most prefer imidazole as the acid binding agent.

The amount of acid binding agent to be used in step A1 will be readily apparent to those skilled in the art, and will mainly be determined by the amount of silylating agent employed. However, suitable amounts of acid binding agent are generally in the region of about 1 to about 2 molar equivalents, preferably about 1 molar equivalent, by reference to the silylating agent.

Any suitable silylating agent may be employed, but we prefer to use a tri-substituted silylating agent of the formula X—$R^1$ (wherein X represents a halogen atom, such as chlorine, bromine or iodide, but preferably chlorine; and $R^1$ is as defined above). Trimethylsilyl chloride, phenyldimethylsilyl chloride and t-butyldimethylsilyl chloride are preferred tri-substituted silylating agents of formula X—$R^1$ and trimethylsilyl chloride is the most preferred silylating agent.

The amount of silylating agent to be used will be readily apparent to those skilled in the art, but will generally be in the range of from about 1 to about 10 molar equivalents, more preferably in the range of from about 1 to about 5 molar equivalents, of the compound of formula (Ia).

There is no particular restriction on the nature of the solvent to be employed, provided that it has no adverse effect on the reaction or on the reagents involved and that it can dissolve the reagents, at least to some extent. Preferred solvents include: aromatic hydrocarbons, such as benzene, toluene and xylene; halogenated hydrocarbons, such as methylene chloride, 1,2-dichloroethane and chloroform; esters, such as ethyl acetate and propyl acetate; amides, such as dimethylformamide and dimethylacetamide; sulfoxides, such as dimethyl sulfoxide; and nitriles, such as acetonitrile and propionitrile. The most preferred solvents are toluene and methylene chloride.

The reaction can take place over a wide range of temperatures, and the precise reaction temperature is not critical to the invention. In general, we find it convenient to perform the reaction at a temperature between about −30° and about 100° C., preferably between about −20° and about 0° C. The time allowed for the reaction is not critical to the present invention, and will generally depend on such factors as temperature, solvent and the nature of the reagents employed. In general, we find it convenient to carry out the reaction for a period of between about 1 and about 5 hours, preferably between about 1 and about 2 hours.

After completion of the reaction, the reaction product can be recovered easily from the reaction mixture by conventional procedures, such as by washing the reaction mixture with water, and then evaporating the washed reaction mixture to dryness under reduced pressure. The product obtained by this procedure can then be used in step A2 without further purification. However, if desired, the product can be further purified by, for example, recrystallization or a chromatographic technique, such as column chromatography, particularly silica gel column chromatography.

In step A2, a compound of formula (IIa) is prepared by oxidizing a compound of formula (Ib), in solution, with a peroxide.

Peroxides which may be used in this step include: peroxy acids, such as m-chloroperbenzoic acid, monoperoxyphthalic acid and peracetic acid; and preparations which yield a suitably active peroxide, such as ethyl chlorocarbonate/hydrogen peroxide. We prefer to sue m-chloroperbenzoic acid as the peroxide. It is also possible to employ a mixture of Oxone and one or more ketones to provide the necessary peroxide, and details are given in the description of step B1 below.

The amount of oxidizing agent used will be readily apparent to those skilled in the art, but will generally be in the range of from about 1 to about 5 molar equivalents, more preferably in the range of from about 1 to about 2 molar equivalents, of the compound of formula (Ib).

There is no particular restriction on the nature of the solvent to be employed, provided that it has no adverse effect on the reaction or on the reagents involved and that it can dissolve the reagents, at least to some extent. Preferred solvents include: aromatic hydrocarbons, such as benzene, toluene and xylene; halogenated hydrocarbons, such as methylene chloride, 1,2-dichloroethane and chloroform; esters, such as ethyl acetate and propyl acetate; amides, such as dimethylformamide and dimethylacetamide; sulfoxides, such as dimethyl sulfoxide; and nitriles, such as acetonitrile and propionitrile. The most preferred solvents are the aromatic hydrocarbons and halogenated hydrocarbons, and the halogenated hydrocarbons, especially methylene chloride and 1,2-dichloroethane are most preferred.

The reaction can take place over a wide range of temperatures, and the precise reaction temperature is not critical to the invention. In general, we find it convenient to perform the reaction at a temperature between about −10° and about 100° C., preferably between about 0° and about 50° C. The time allowed for the reaction is not critical to the present invention, and will generally depend on such factors as temperature, solvent and the nature of the reagents employed. In general, we find it convenient to carry out the reaction for a period of between about 10 minutes and about 5 hours, preferably between about 30 minutes and about 2 hours.

After completion of the epoxidization reaction, the desired product can be recovered easily from the reaction mixture by conventional procedures. For example, an aqueous solution of sodium thiosulfate can be added to the reaction mixture to decompose excess peroxy acid, followed by washing the reaction mixture with an aqueous solution of sodium hydrogencarbonate and water, in that order, and then evaporating the solvent under reduced pressure. The product obtained by this procedure can then be used in step A3 without further purification. However, if desired, the product can be further purified by, for example, recrystallization or a chromatographic technique, such as column chromatography, particularly silica gel column chromatography.

In step A3, a compound of formula (IIIa) is prepared by reacting a compound of formula (IIa), in solution, with a silylating agent in the presence of a base.

Any suitable silylating agent may be employed in this step, and appropriate silylating agents will be readily apparent to those skilled in the art. We find it convenient to use tri-substituted silyl triflates having the formula $CF_3SO_2OR^7R^8R^9$ (wherein $R^7$, $R^8$ and $R^9$ are as defined above), such as trimethyl triflate, phenyldimethyl triflate and t-butyldimethyl triflate, preferably t-butyldimethyl triflate. Where any of $R^7$, $R^8$ and $R^9$ is an aryl group or an aralkyl group, and especially where the resulting tri-substituted silyl group is not commercially available, then triflates containing these groups can be prepared in accordance with the method described in Tetrahedron Letters (1981), 22, 3455.

The amount of silylating agent used will be readily apparent to those skilled in the art, but will generally be in the range of from about 1.0 to about 10 molar equivalents, more preferably in the range of from about 1.5 to about 3.0 molar equivalents, of the compound of formula (IIa).

Any suitable base may be used in this step, and appropriate bases will be readily apparent to those skilled in the art. In general, there is no particular restriction on the base, provided that it does not have an unduly adverse effect on the reaction. We find it convenient to use a base selected from 2,6-lutidine, pyridine, 2,6-di-t-butylpyridine and triethylamine, and we prefer to use 2,6-lutidine.

The amount of base to be used will be readily apparent to those skilled in the art, and will mainly be determined by the amount of silylating agent employed. However, suitable amounts of base are generally in the region of from about 1 to about 10 molar equivalents, preferably from about 2 to about 5 molar equivalent, by reference to the silylating agent.

There is no particular restriction on the nature of the solvent to be employed, provided that it has no adverse effect on the reaction or on the reagents involved and that it can dissolve the reagents, at least to some extent. Preferred solvents include: aromatic hydrocarbons, such as benzene, toluene and xylene; halogenated hydrocarbons, such as methylene chloride, 1,2-dichloroethane and chloroform; esters, such as ethyl acetate and propyl acetate; amides, such as dimethylformamide and dimethylacetamide; sulfoxides, such as dimethyl sulfoxide; and nitriles, such as acetonitrile and propionitrile. The most preferred solvents are the aromatic hydrocarbons and halogenated hydrocarbons, particularly toluene and methylene chloride.

The reaction can take place over a wide range of temperatures, and the precise reaction temperature is not critical to the invention. In general, we find it convenient to perform the reaction at a temperature between about −50° and about 100° C., preferably between about −30° and about 50° C. The time allowed for the reaction is not critical to the present invention, and will generally depend on such factors as temperature, solvent and the nature of the reagents employed. In general, we find it convenient to carry out the reaction for a period of between about 7 and about 48 hours, preferably between about 12 and about 24 hours.

After completion of the reaction, the reaction product can be recovered easily from the reaction mixture by conventional procedures. For example, the reaction mixture can be washed with 1M aqueous hydrochloric acid, water, an aqueous solution of sodium hydrogencarbonate and water, in that order, followed by evaporation of the solvent under reduced pressure. The product obtained by this procedure can then be used directly without further purification. However, if desired, the product can be further purified by, for example, recrystallization or a chromatographic technique, such as column chromatography, particularly silica gel column chromatography.

Step A4 is optional. In this step, a compound of formula (IIIc) is prepared by deprotecting a compound of formula (IIIa), in a solvent, in the presence of an acid.

There is no particular restriction on the acid which can be used in this step, and suitable acids will be readily apparent to those skilled in the art. Examples of acids which can be used in this step include: mineral acids, such as hydrochloric acid, hydrobromic acid and sulfuric acid, preferably hydrochloric acid; aliphatic carboxylic acids, such as formic acid and trifluoroacetic acid, preferably trifluoroacetic acid; monoalkylsulfuric acids, such as monomethylsulfuric acid and monoethylsulfuric acid; sulfinic acids, such as benzenesulfinic acid; and sulfonic acids, such as methanesulfonic acid and p-toluenesulfonic acid. In general, we find it convenient to use the acid in great excess.

There is no particular restriction on the nature of the solvent to be employed, provided that it has no adverse effect on the reaction or on the reagents involved and that it can dissolve the reagents, at least to some extent. Preferred solvents include: aromatic hydrocarbons, such as benzene, toluene and xylene; halogenated hydrocarbons, such as dichloromethane, 1,2-dichloroethane and chloroform; esters such as ethyl acetate and propyl acetate; ethers, such as diethyl ether, tetrahydrofuran, dioxane and dimethoxyethane; and nitriles such as acetonitrile. The most preferred solvents are toluene and dichloromethane.

The reaction can take place over a wide range of temperatures, and the precise reaction temperature is not critical to the invention. In general, we find it convenient to perform the reaction at a temperature between about $-10°$ and about $50°$ C., preferably between about $20°$ and about $30°$ C. The time allowed for the reaction is not critical to the present invention, and will generally depend on such factors as temperature, solvent and the nature of the reagents employed. In general, we find it convenient to carry out the reaction for a period of between about 30 minutes and about 5 hours, preferably between about 1 and about 2 hours.

After completion of the reaction, the reaction product can be recovered easily from the reaction mixture by conventional procedures. For example, the reaction mixture can be washed with water, an aqueous solution of sodium hydrogencarbonate and water, in that order, followed by evaporation of the solvent under reduced pressure. The product obtained by this procedure can then be used directly without further purification. However, if desired, the product can be further purified by, for example, recrystallization or a chromatographic technique, such as column chromatography, particularly silica gel column chromatography.

Reaction Scheme B

In step B1, a compound of formula (IIb) is prepared by reacting a compound of formula (Ia) with a peroxide in the presence of a solvent.

The peroxide may be provided by a mixture of Oxone (trade mark, potassium peroxymonosulfate: $2KHSO_5 \cdot KHSO_4 \cdot K_2SO_4$, Du Pont Japan Limited) and one or more ketones.

The amount of potassium peroxymonosulfate used is not critical to the present invention provided that, in combination with the ketone(s), sufficient peroxide is generated to enable the epoxidation reaction to proceed. In general, we find it convenient to use potassium peroxymonosulfate in an amount of from about 0.5 to about 5.0 molar equivalent, preferably from about 0.7 to about 1.5 molar equivalent of the compound of formula (Ia).

The nature of the ketones used is not critical to the present invention provided that, in combination with potassium peroxymonosulfate, sufficient peroxide is generated to enable the epoxidation reaction to proceed. Suitable ketones include acetone, methyl ethyl ketone, cyclohexanone, trifluoroacetone and chloroacetone, preferably acetone.

The ketone(s) will generally be used in great excess so that, in effect, they can also act as the solvent. However, where other solvents are used, there is no particular restriction on the nature of the solvent, provided that it has no adverse effect on the reaction or on the reagents involved and that it can dissolve the reagents, at least to some extent. Preferred solvents include: a mixture of ketones, such as acetone, methyl ethyl ketone, cyclohexanone, trifluoroacetone and chloroacetone together with one or more aromatic hydrocarbons or halogenated hydrocarbons as described above with respect to step A1. We prefer that the solvent is either a mixture of acetone and benzene, acetone and toluene, acetone and methylene chloride or acetone and 1,2-dichloroethane, we most prefer that the solvent is a mixture of acetone and methylene chloride.

Where a mixed solvent is employed, then a suitable ratio of components (v/v) is in the region of about 0.5:2, and is preferably in the region of about 0.9:1.2.

We prefer to carry out the reaction in a bi-phasic reaction mixture, using a mixed solvent as defined above together with a phosphate buffer (pH 7.0 to 8.0).

The reaction can take place over a wide range of temperatures, and the precise reaction temperature is not critical to the invention. In general, we find it convenient to perform the reaction at a temperature between about $-10°$ and about $100°$ C., preferably between about $0°$ and about $50°$ C. The time allowed for the reaction is not critical to the present invention, and will generally depend on such factors as temperature, solvent and the nature of the reagents employed. In general, we find it convenient to carry out the reaction for a period of between about 10 minutes and about 5 hours, preferably between about 30 minutes and about 2 hours.

We have found that the best results are generally obtained by maintaining the reaction at a substantially constant pH of between about 7.5 and 8.0 by adding, as required, an aqueous solution of an alkali, such as potassium hydroxide or sodium hydroxide.

After completion of the reaction, the reaction product can be recovered easily from the reaction mixture by conventional procedures. For example, an aqueous solution of sodium thiosulfate can be added to the reaction mixture to decompose excess peroxide, followed by washing the reaction mixture with an aqueous solution of sodium hydrogencarbonate and water, in that order, and then evaporating the solvent under reduced pressure. The product obtained by this procedure can then be used in step B2 without further purification. However, if desired, the product can be further purified by, for example, recrystallization or a chromatographic technique, such as column chromatography, particularly silica gel column chromatography.

In step B2, a compound of formula (IIIb) is prepared by reacting a compound of formula (IIb) with a silylating agent in the presence of a solvent.

In general, the reagents and conditions described above for step A3 are also appropriate to step B2. Although the reaction temperature is not critical, the preferred reaction temperature is between about $-10°$ C. and about $100°$ C., more preferably between about $0°$ C. and about $5°$ C. The reaction product may be recovered by similar procedures to those described in relation to step A3.

A further step B3 (not shown) may be performed, if desired, to deprotect the compound of formula (IIIb) to yield a compound of formula (IIId) wherein both $R^5$ and $R^{6'}$ each represent a hydrogen atom. Step B3 may be performed in a similar manner as for step A4 above. However, step B3 will generally be unnecessary, as the reaction to produce a compound of formula (VIIa) can proceed when the 15-position is protected.

A compound of formula (VIIa):

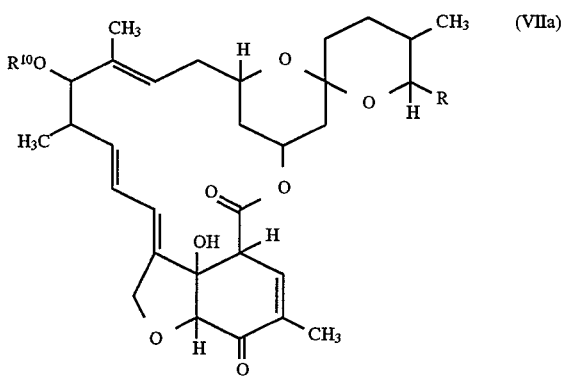

(wherein R and $R^{10}$ are as defined above) may be prepared from any of compounds of the formulae (IIIa), (IIIb) or (IIIc) in conventional fashion by reaction with an alcohol of formula $R^{10}OH$ in the presence of an acid.

Hydrogenation of the resulting compound of formula (VIIa) by conventional procedures, such as is described in Japanese Patent Application Sho-62-70379, then yields a compound of formula (IVa).

The compound of formula (IVa) can then be used directly as an anthelmintic, for example, or can be further derivatized, such as is described in European Patent Publication No. 357 460.

The present invention is described below in more detail by way of the accompanying Examples, but it will be appreciated that the present invention is not limited thereto.

EXAMPLE 1

5-Oxo-7-deoxy-7-trimethylsilyloxymilbemycin $A_4$

A Compound of Formula (I)

1.36 g of imidazole were dissolved in 30 ml of methylene chloride, and 2.41 ml of trimethylsilyl chloride was added to the resulting solution under a nitrogen stream. The resulting mixture was then cooled to $-10°\pm2°$ C.

A solution of 2.67 g of 5-oxomilbemycin $A_4$ in 30 ml methylene chloride was added to the cooled mixture, and the resulting mixture was allowed to react with stirring at $-°\pm2°$ C. for about 2 hours. After this time, the reaction mixture was washed with water and evaporated to dryness under reduced pressure to afford 2.67 g (yield 96.1%) of the title compound as an amorphous solid.

Mass spectrum (m/z): 612 ($M^+C_{35}H_{52}O_7Si$).

Nuclear Magnetic Resonance Spectrum ($CDCl_3$, 270 MHz) δ ppm:
3.87 (1H, singlet),
4.71 (2H, singlet),
5.01–5.05 (1H, multiplet),
6.82–6.83 (1H, multiplet).

Infrared Absorption Spectrum (KBr) $\nu_{max}$ cm$^{-1}$: 1743, 1683.

EXAMPLE 2

5-Oxo-7-deoxy-7-trimethylsilyloxy-14,15-epoxy-milbemycin $A_4$

A Compound of Formula (IIa)

1. 6.68 g of 5-oxo-7-deoxy-7-trimethylsilyloxymilbemycin $A_4$ (prepared as described in Example 1) were dissolved in 50 ml of methylene chloride, and the resulting solution was cooled to a temperature of between 0° and 5° C. A solution of 3.02 g of m-chloroperbenzoic acid in 30 ml of methylene chloride was added to the cooled solution, and the reaction was then allowed to proceed with stirring for 2 hours, at a temperature of between 0° and 5° C. After this time, the insolubles were removed by filtration and excess m-chloroperbenzoic acid in the filtrate was decomposed using 30 ml of an aqueous solution of 10% w/v sodium thiosulfate. The reaction solution was then washed first with a 5% w/v aqueous solution of sodium hydrogencarbonate then with water, and was subsequently evaporated to dryness under reduced pressure to afford 6.61 g (yield 96.5%) of the title compound as an amorphous solid.

Mass spectrum (m/z): 628 ($M^+C_{35}H_{52}O_8Si$).

Nuclear Magnetic Resonance Spectrum ($CDCl_3$, 270 MHz) δ ppm:
2.65 (1H, doublet, J=10.0 Hz),
3.75–3.85 (1H, multiplet),
3.90 (1H, singlet),
4.69–4.80 (2H, multiplet),
6.84–6.85 (1H, multiplet).

Infrared Absorption Spectrum (KBr) $\nu_{max}$ cm$^{-1}$: 1743, 1681.

2. 3.06 g of 5-oxo-7-deoxy-7-trimethylsilyloxymilbemycin $A_4$ (prepared as described in Example 1) were dissolved in 24 ml of methylene chloride. 24 ml of a phosphate buffer (an aqueous solution of 44 mM $KH_2PO_4$ and 330 mM $Na_2HPO_4$, pH 7.5) and 24 ml of acetone were added to the resulting solution, which was then cooled to a temperature of between 0° and 5° C. After cooling, a solution of 3.04 g of potassium peroxymonosulfate (Oxone, Trade Mark of Du Pont) in 24 ml of a phosphate buffer (pH 7.5, as defined above) was added in a dropwise fashion over a period of about 30 minutes. During this time, a 3M aqueous solution of potassium hydroxide was added, as required, in order to maintain the pH in the region of 7.5 to 8.0. The resulting mixture was allowed to react at this pH at a temperature of between 0° and 5° C. for about 2 hours. After this time, 30 ml of an aqueous solution of 10% w/v sodium thiosulfate was added to the reaction mixture in order to decompose any excess peroxide, and the reaction mixture was then washed with a 5% w/v aqueous solution of sodium hydrogencarbonate and water, in that order, and subsequently evaporated to dryness under reduced pressure to afford 3.08 g (yield 98.0%) of the title compound as an amorphous solid.

Mass spectrum (m/z): 628 ($M^+C_{35}H_{52}O_8Si$).

Nuclear Magnetic Resonance Spectrum ($CDCl_3$, 270 MHz) δ ppm:
2.65 (1H, doublet, J=10.0 Hz),
3.75–3.85 (1H, multiplet),
3.90 (1H, singlet),
4.69–4.80 (2H, multiplet),
6.84–6.85 (1H, multiplet).

Infrared Absorption Spectrum (KBr) $\nu_{max}$ cm$^{-1}$: 1743, 1681.

EXAMPLE 3

5-Oxo-14,15-epoxymilbemycin $A_4$

A compound of Formula (IIb)

24 ml of a phosphate buffer (pH 7.5, as defined in Example 2 above) and 24 ml of acetone were added to a solution of 3.06 g of 5-oxomilbemycin $A_4$ in 24 ml of methylene chloride, and the resulting mixture was cooled to a temperature of between 0° and 5° C. A solution of 3.04 g of Oxone in 24 ml of a phosphate buffer (pH 7.5, as defined in Example 2 above) was added in a dropwise fashion over a period of about 30 minutes. During this time, a 3M aqueous solution of potassium hydroxide was added, as required, in order to maintain the pH in the region of 7.5 to 8.0. The resulting mixture was allowed to react at this pH at a temperature of between 0° and 5° C. for about 2 hours. After this time, 30 ml of an aqueous solution of 10% w/v sodium thiosulfate was added to the reaction mixture in order to decompose any excess peroxide, and the reaction mixture was then washed with a 5% w/v aqueous solution of sodium hydrogencarbonate and water, in that order, and subsequently evaporated to dryness under reduced pressure to afford 3.08 g (yield 98.0%) of the title compound as an amorphous solid.

Mass spectrum (m/z): 556 ($M^+C_{34}H_{44}O_8$).

Nuclear Magnetic Resonance Spectrum ($CDCl_3$, 270 MHz) δ ppm:
2.60 (1H, doublet, J=9.2 Hz),
3.07 (1H, doublet of triplets, J=2.4, 9.3 Hz),
3.53 (1H, singlet),
3.58–3.59 (1H, multiplet),
3.88 (1H, singlet),
6.62 (1H, multiplet).

Infrared Absorption Spectrum (KBr) $v_{max}$ cm$^{-1}$: 3479, 1740, 1683.

EXAMPLE 4

5-Oxo-7,15-bistrimethylsilyloxy-7-deoxy-$\Delta^{13,14}$-milbemycin $A_4$

A Compound of Formula (IIIa)

3.14 g of 5-oxo-7-deoxy-7-trimethylsilyloxy-14,15-epoxymilbemycin $A_4$ (prepared as described in Example 2) were dissolved in 35 ml of toluene. The resulting solution was cooled to a temperature of between 0° and 5° C., after which 2.02 ml of 2,6-lutidine and 1.67 ml of trimethylsilyl triflate (prepared as described in Preparation 1) were added. The resulting mixture was then stirred at a temperature of between 0° and 5° C. for 6 to 7 hours in a nitrogen stream. After this time, the mixture was left to stand overnight at a temperature of between 0° and 5° C. Subsequently, the reaction mixture was washed with: 1M hydrochloric acid; water; a 5% w/v aqueous solution of sodium hydrogencarbonate; and water, in that order. The washed reaction mixture was then evaporated to dryness under reduced pressure to afford 3.02 g (yield 89.2%) of the title compound as an amorphous solid. The powder thus obtained was further purified by silica gel column chromatography (using methylene chloride as eluent) to afford 2.87 g (yield 82%) of the title compound as an amorphous solid.

Mass spectrum (m/z): 700 ($M^+C_{38}H_{60}O_8Si_2$).

Nuclear Magnetic Resonance Spectrum ($CDCl_3$, 270 MHz) δ ppm:
3.94 (1H, singlet),
3.94–3.99 (1H, multiplet),
5.04 (1H, doublet, J=9.3 Hz),
6.74–6.75 (1H, multiplet).

Infrared Absorption Spectrum (KBr) $v_{max}$ cm$^{-1}$: 1746, 1684.

EXAMPLE 5

5-Oxo-7-deoxy-7-trimethylsilyloxy-15-phenyldimethyl-silyloxy-$\Delta^{13,14}$-milbemycin $A_4$

A Compound of Formula (IIIa)

2.0 g of 5-oxo-7-deoxy-7-trimethylsilyloxy-14,15-epoxymilbemycin $A_4$ (prepared as described in Example 2) were dissolved in 50 ml of toluene, and the resulting solution was cooled to a temperature of between 0° and 5° C. under a nitrogen stream. 1.34 ml of phenyldimethylsilyl triflate (prepared as described in Preparation 1) and 1.5 ml of 2,6-lutidine were added to the cooled solution, and the reaction was allowed to proceed overnight at a temperature of between 0° and 5° C. The reaction mixture was then washed with: 1M aqueous hydrochloric acid; water; a 5% w/v aqueous solution of sodium hydrogencarbonate; and water, in that order, and was then evaporated to dryness under reduced pressure. The residue was purified by silica gel column chromatography (using methylene chloride as the eluent) to afford 3.4 g (yield 70%) of the title compound as an amorphous solid.

Mass spectrum (m/z): 762 ($M^+C_{43}H_{62}O_8Si_2$).

Nuclear Magnetic Resonance Spectrum ($CDCl_3$, 270 MHz) δ ppm:
3.42 (1H, triplet, J=2.4 Hz),
3.93 (1H, singlet),
3.90–3.95 (1H, multiplet),
6.72–6.74 (1H, multiplet),
7.62–7.63 (5H, multiplet).

Infrared Absorption Spectrum ($CHCl_3$) $v_{max}$ cm$^{-1}$: 1730, 1670.

EXAMPLE 6

5-Oxo-15-t-butyldimethylsilyloxy-$\Delta^{13,14}$-milbemycin $A_4$

A Compound of Formula (IIIb)

5.0 g of 5-oxo-14,15-epoxymilbemycin $A_4$ (prepared as described in Example 3) were dissolved in 25 ml of toluene, and the solution was cooled to a temperature of between 0° and 5° C. 2.02 ml of 2,6-lutidine, 10.5 ml of triethylamine and 4.05 ml of t-butyldimethylsilyl triflate were added to the cooled solution, which was then stirred at a temperature of between 0° and 5° C. for 6 to 7 hours under a nitrogen stream, after which time the mixture was left to stand overnight at a temperature of between 0° and 5° C. After this time, the reaction mixture was washed with 1M aqueous hydrochloric acid, water, a 5% w/v aqueous solution of sodium hydrogen-carbonate, and water, in that order, followed by evaporation to dryness under reduced pressure to afford 3.02 g (yield 89.2%) of the target compound. The powder thus obtained was purified by silica gel column chromatography (using methylene chloride as the eluent) to afford 5.12 g (yield 85%) of the title compound as an amorphous solid.

Mass spectrum (m/z): 670 ($M^+C_{38}H_{59}O_8Si$).

Nuclear Magnetic Resonance Spectrum ($CDCl_3$, 270 MHz) δ ppm:

2.97 (1H, doublet of triplets, J=1.9, 9.6 Hz),
3.52–3.54 (1H, multiplet),
3.93 (1H, singlet),
3.96 (1H, doublet of doublets, J=6.0, 9.5 Hz), 6.54–6.55 (1H, multiplet).

Infrared Absorption Spectrum (KBr) $v_{max}$ cm$^{-1}$: 3486, 1716, 1689.

EXAMPLE 7

5-Oxo-15-trimethylsilyloxy-$\Delta^{13,14}$-milbemycin A$_4$

A Compound of Formula (IIIb)

10.0 g of 5-oxo-14,15-epoxymilbemycin A$_4$ (prepared as described in Example 3) were dissolved in 100 ml of toluene, and the solution was cooled to a temperature of between 10° and 15° C. 6.2 ml of 2,67-lutidine and 6.5 mg of trimethylsilyl triflate were added to the cooled solution, which was then stirred for an hour under a nitrogen stream to effect the reaction. After this time, the reaction mixture was washed with 1M aqueous hydrochloric acid, water, a 5% w/v aqueous solution of sodium hydrogencarbonate, and water, in that order, and was then evaporated to dryness under reduced pressure to afford 10.13 g (yield 90.0%) of the target compound. The powder thus obtained was purified by silica gel column chromatography (using methylene chloride as the eluent) to afford 9.46 g (yield 84%) of the title compound as an amorphous solid.

Mass spectrum (m/z): 628 (M$^+$C$_{35}$H$_{52}$O$_8$Si).

Nuclear Magnetic Resonace Spectrum (CDCl$_3$, 270 MHz) δ ppm:
2.97 (1H, doublet of triplets, J=2.1, 9.6 Hz),
3.52–3.54 (1H, multiplet),
3.80–3.90 (1H, multiplet),
3.93 (1H, singlet),
3.96 (1H, doublet of doublets, J=6.0, 9.5 Hz),
6.54–6.55 (1H, multiplet).

Infrared Absorption Spectrum (KBr) $v_{max}$ cm$^{-1}$: 3500, 1720, 1675.

EXAMPLE 8

5-Oxo-7-deoxy-7-trimethylsilyloxy-15-hydroxy-$\Delta^{13,14}$-milbemycin A$_4$

A Compound of Formula (IIIc)

3.0 g of 5-oxo-7,15-bistrimethylsilyloxy-7-deoxy-$\Delta^{13,14}$-milbemycin A$_4$ was dissolved in 20 ml of ethyl acetate, and 20 ml of 1M aqueous hydrochloric acid was added to the resulting solution at a temperature of between 20° and 25° C., followed by stirring for 1.5 hours. After this time, the reaction mixture was washed with water, a 5% w/v aqueous solution of sodium hydrogencarbonate and water, in that order, and was then evaporated to dryness under reduced pressure. The residue was purified by silica gel column chromatography (using ethyl acetate/n-hexane in a ratio of 1/1.2 by volume as the eluent) to afford 1.41 g (yield 52.4%) of the title compound as an amorphous solid.

Mass spectrum (m/z): 628 (M$^+$C$_{35}$H$_{52}$O$_8$Si).

Nuclear Magnetic Resonance Spectrum (CDCl$_3$, 270 MHz) δ ppm:
3.94 (1H, singlet),
4.08 (1H, doublet of doublets, J=3.9 Hz, 10.7 Hz),
5.16 (1H, doublet, J=10.7 Hz),
6.74–6.76 (1H, multiplet).

Infrared Absorption Spectrum (KBr) $v_{max}$ cm$^{-1}$: 3513, 1745, 1681.

EXAMPLE 9

5-Oxo-13-{2-[4-(N-methanesulfonyl-N-methylamino)-phenyl]ethoxy}milbemycin A$_4$

A Compound of Formula (VII)

1. 3.02 g of 5-oxo-7,15-bistrimethylsilyloxy-7-deoxy-$\Delta^{13,14}$-milbemycin A$_4$ (prepared as described in Example 4) and 1.96 g of 2-{4-(N-methanesulfonyl-N-methylamino) phenyl}ethyl alcohol were dissolved in 60 ml of methylene chloride, and the resulting solution was cooled to about 15° C. 0.19 ml of trifluoromethanesulfonic acid was added to the cooled solution, which was then stirred at a temperature of between 18° and 20° C. for about 1 hour under a nitrogen stream. The reaction mixture was washed with a 5% w/v aqueous solution of sodium chloride, a 5% w/v aqueous solution of sodium hydrogencarbonate, and water, in that order, and was then evaporated to dryness under reduced pressure. The residue was purified by silica gel column chromatography (using ethyl acetate/n-hexane in a ratio of 1:1.5 by volume as the eluent) to afford 2.98 g (yield 90% of the title compound as an amorphous solid.

Mass spectrum (m/z): 7.67 (M$^+$C$_{42}$H$_{57}$O$_{10}$NS).

Nuclear Magnetic Resonance Spectrum (CDCl$_3$, 270 MHz) δ ppm:
1.89 (3H, multiplet),
2.82 (3H, singlet),
3.22 (1H, doublet, J=9.8 Hz),
3.30 (3H, singlet),
3.85 (1H, singlet),
6.55 (1H, multiplet).

Infrared Absorption Spectrum (KBr) $v_{max}$ cm$^{-1}$: 3475, 1737, 1682.

2. 2.34 g of 5-oxo-7,15-bistrimethylsilyloxy-7-deoxy-$\Delta^{13,14}$-milbemycin A$_4$ (prepared as described in Example 4) and 1.51 g of 2-{4-(N-methanesulfonyl-N-methylamino) phenyl}ethyl alcohol were dissolved in 31 ml of methylene chloride. 0.49 g of methanesulfonic acid was added to the resulting solution, and the mixture stirred under reflux at about 40° C. for between 1 and 1.5 hours under a nitrogen stream. The reaction mixture was then washed with a 5% w/v aqueous solution of sodium chloride, a 5% w/v aqueous solution of sodium hydrogencarbonate and water, in that order, followed by evaporation to dryness under reduced pressure. The residue was purified by silica gel column chromatography (using ethyl acetate/n-hexane in a ratio of 1:1.5 by volume as the eluent) to afford 2.33 g (yield 91%) of the title compound as an amorphous solid.

EXAMPLE 10

5-Oxo-13-{2-[4-(N-methanesulfonyl-N-methylamino)-phenyl]ethoxy}milbemycin A$_4$

A Compound of Formula (VII)

5.00 g of 5-oxo-15-t-butyldimethylsilyloxy-$\Delta^{13,14}$-milbemycin A$_4$ (prepared as described in Example 6) and 3.39 g of 2-[4-(N-methanesulfonyl-N-methylamino)phenyl] ethyl alcohol were dissolved in 100 ml of methylene chloride, and the resulting solution was cooled to about 15° C. 1.36 ml of trifluoromethanesulfonic acid were added to the cooled solution, which was then stirred at a temperature of between 18° and 20° C. for about 1 hour under a nitrogen stream. After this time, the reaction mixture was washed with a 5% w/v aqueous solution of sodium chloride, a 5% w/v aqueous solution of sodium hydrogencarbonate and water, in that order, followed by evaporation to dryness under reduced pressure. The residue was purified by silica gel column chromatography (using ethyl acetate/n-hexane in a ratio of 1:1.5 by volume as the eluent) to afford 2.98 g (yield 90%) of the title compound as an amorphous solid.

Mass spectrum (m/z): 767 ($M^+C_{42}H_{57}O_{10}NS$).

Nuclear Magnetic Resonance Spectrum ($CDCl_3$, 270 MHz) δ ppm;
1.89 (3H, multiplet),
2.82 (3H, singlet),
3.22 (1H, doublet, J=9.8 Hz),
3.30 (3H, singlet),
3.85 (1H, singlet),
6.55 (1H, multiplet).

Infrared Absorption Spectrum (KBr) $v_{max}$ $cm^{-1}$: 3475, 1737, 1682.

EXAMPLE 11

13-{2-[4-(N-Methanesulfonyl-N-methylamino)phenyl]-ethoxy}milbemycin $A_4$

A Compound of Formula (IV)

0.344 g of 5-oxo-13-{2-[4-(N-methanesulfonyl-N-methylamino)phenyl]ethoxy}milbemycin $A_4$ (prepared as described in either of Examples 9 and 10) was dissolved in 7.4 ml of methanol and 3.7 ml of tetrahydrofuran. The resulting solution was cooled to between −40° and −50° C., when 0.019 g of sodium borohydride and a catalytic amount of boron trifluoride diethyl etherate were added, after which the mixture was stirred for one hour. After this time, 50 ml of ethyl acetate were added to the reaction mixture, which was then washed twice with water, dried over anhydrous sodium sulfate and evaporated to dryness under reduced pressure. The residue was purified by column chromatography (ODS, 85% aqueous acetonitrile used as eluent), and then recrystallized from ethyl acetate/hexane (in a ratio of 1:4 v/v) to afford 0.307 g (yield 90.0%) of the title compound as an amorphous solid.

Mass spectrum (m/z): 769 ($M^+$, $C_{42}H_{59}NO_{10}S$).

Nuclear Magnetic Resonance Spectrum ($CDCl_3$, 270 MHz) δ ppm:
1.87 (3H, singlet),
2.82 (3H, singlet),
3.21 (1H, doublet, J=7.6 Hz),
3.30 (3H, singlet),
3.95 (1H, doublet, J=6.3 Hz).

EXAMPLE 12

13-{2-[4-(N-Methanesulfonyl-N-methylamino)phenyl]-ethoxy}milbemycin $A_3$

A Compound of Formula (IV)

a) 5Oxo-14,15-epoxymilbemycin $A_3$

Following a procedure similar to that of Example 3, but using 3.0 g (5.55 mmol) of 5-oxomilbemycin $A_3$ as the starting material, the title compound was obtained in an amount of 2.9 g (yield 95%, 5.27 mmol) as an amorphous solid.

Mass spectrum (m/z): 542 ($M^+C_{33}H_{42}O_8$).

Nuclear Magnetic Resonance Spectrum ($CDCl_3$, 270 MHz) δ ppm:
2.60 (1H, doublet, J=9.2 Hz),
3.53 (1H, singlet),
3.58–3.59 (1H, multiplet),
3.88 (1H, singlet),
6.62 (1H, multiplet).

Infrared Absorption Spectrum (KBr) $v_{max}$ $cm^{-1}$: 3480, 1740, 1685.

b) 5-Oxo-15-t-butyldimethylsilyloxy-$\Delta^{13,14}$-milbemycin $A_3$

Following a procedure similar to that of Example 6, but using 2.0 g (3.59 mmol) of 5-oxo-14,15-epoxymilbemycin $A_3$ (prepared as described in a above), the title compound was afforded in an amount of 1.9 g (yield 80%, 2.87 mmol) as an amorphous solid.

Mass spectrum (m/z): 656 ($M^+C_{37}H_{57}O_8Si$).

Nuclear Magnetic Resonance Spectrum ($CDCl_3$, 270 MHz) δ ppm:
3.52–3.54 (1H, multiplet),
3.93 (1H, singlet),
3.96 (1H, doublet of doublets, J=6.0, 9.5 Hz),
6.54–6.55 (1H, multiplet).

Infrared Absorption Spectrum (KBr) $v_{max}$ $cm^{-1}$: 3486, 1720, 1690.

c) 5-Oxo-13-{2-[4(N-methanesulfonyl-N-methylamino)-phenyl]ethoxy}milbemycin $A_3$ 11.0 g of 2-{4-(N-methanesulfonyl-N-methylamino)-phenyl}ethyl alcohol were dissolved in 100 ml of methylene chloride, and 1.40 ml of trifluoromethanesulfonic acid were added to the resulting solution, which was then stirred at room temperature for 5 minutes. 5.81 g of 5-oxo-15-t-butyldimethylsilyloxy-$\Delta^{13,14}$-milbemycin $A_3$ (prepared as described in b above) was added to the resulting mixture, which was then stirred at room temperature for 30 minutes. After this time, 500 ml of ethyl acetate were added to the reaction mixture, which was then washed with water, a 4% w/v aqueous solution of sodium hydrogencarbonate and water, in that order, dried over anhydrous sodium sulfate and subsequently evaporated to dryness under reduced pressure. The residue was recrystallized from a mixture of ethyl acetate/cyclohexane (in a ratio of 1:4 v/v) and the precipitated crystals were removed by filtration. The filtrate was purified by silica gel column chromatography (using ethyl acetate/hexane in a ratio of 3:7 by volume) to afford 7.42 g of the target compound (yield 91.9%).

Nuclear Magnetic Resonance spectrum ($CDCl_3$, 270 MHz) δ ppm:
1.89 (3H, multiplet),
2.82 (3H, singlet),
3.23 (1H, doublet, J=9.8 Hz),
3.30 (3H, singlet),
3.86 (1H, singlet),
6.55 (1H, multiplet).

d) 13-{2-[4-(N-methanesulfonyl-N-methylamino)phenyl]-ethoxy}milbemycin $A_3$

All of the compound obtained in c) above was dissolved in a mixture of 80 ml of methanol and 40 ml of tetrahydrofuran. The resulting solution was cooled to between −40° and −50° C., when 0.36 g of sodium borohydride and a catalytic amount of boron trifluoride diethyl etherate were added, after which the mixture was stirred for 3.5 hours. After this time, 500 ml of ethyl acetate were added to the reaction mixture, which was then washed twice with water, dried over anhydrous sodium sulfate and evaporated to dryness under reduced pressure. The residue was purified by column chromatography (ODS, eluted with 85% v/v aqueous acetonitrile) to afford 6.74 g (yield 90.6%) of the title compound as an amorphous solid.

Mass spectrum (m/z): 7.55 ($M^+$, $C_{41}H_{57}NO_{10}S$).

Nuclear Magnetic Resonance Spectrum ($CDCl_3$, 270 MHz) δ ppm:
1.87 (3H, singlet),
2.82 (3H, singlet),
3.21 (1H, doublet, J=7.6 Hz),
3.30 (3H, singlet),
3.95 (1H, doublet, J=6.3 Hz).

PREPARATION 1

Phenyldimethylsilyl triflate

Phenyldimethylsilyl triflate was prepared by cooling 5 ml of phenyldimethylsilyl chloride to a temperature between 0° and 5° C., and then adding 4.2 ml of trifluoromethanesulfonic acid in a dropwise fashion over a period of about 30 minutes. The resulting mixture was then stirred at a temperature of between 0° and 5° C. for about 6 hours, and subsequently left to stand, with cooling, overnight. The resulting preparation could be used without any further purification.

What is claimed is:

1. A process for the preparation of a compound of formula (IIIb):

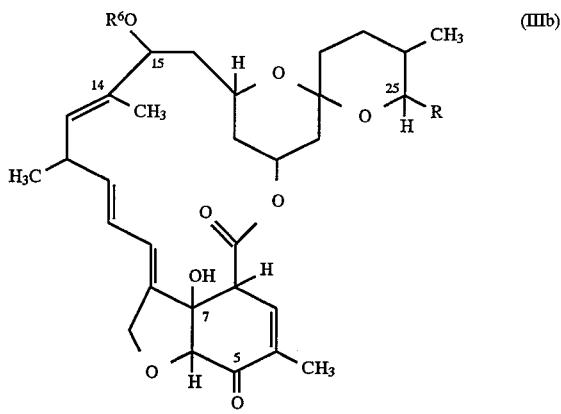

in which R represents a methyl group, an ethyl group, an isopropyl group or a sec-butyl group, $R^6$ represents a hydroxy-protecting group;

which process comprises subjecting a compound of formula (IIb):

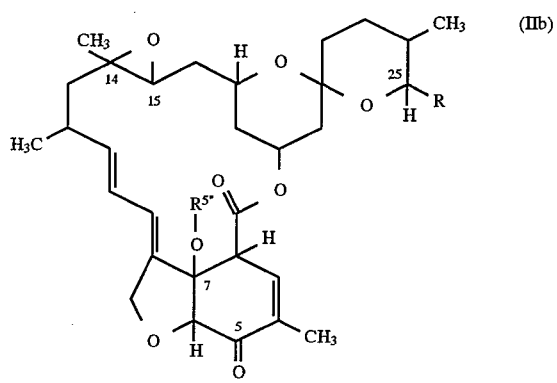

wherein R is as defined above and $R^{5"}$ is a hydrogen atom;

to a ring-opening etherification reaction.

2. The process of claim 1, wherein $R^6$ represents a group of formula $—SiR^7R^8R^9$, wherein $R^7$, $R^8$ and $R^9$ are each independently selected from the group consisting of alkyl groups having from 1 to 6 carbon atoms, aryl and aralkyl groups.

3. The process of claim 1, wherein $R^6$ represents a trimethylsilyl group.

4. The process of claim 1, wherein R represents a methyl group or an ethyl group.

5. The process of claim 1 wherein the ring opening etherification comprises reacting the compound of formula (IIb) with a silylating agent in the presence of a base.

6. The process of claim 5, wherein the silylating agent is a trisubstituted silyl triflate having the formula $CF_3SO_2OR^7R^8R^9$ wherein $R^7$, $R^8$ and $R^9$ are each independently selected from the group consisting of alkyl groups having 1–6 carbon atoms, aryl and aralkyl group.

7. The process of claim 6, wherein the silylating agent is trimethyl triflate, phenyldimethyl triflate or t-butyldimethyl triflate.

8. The process of claim 6, wherein the silylating agent is used in an amount of 1.0 to 10.0 molar equivalents of the compound of formula (IIb); the base is used in an amount of about 1 to 10 molar equivalents referred to the silylating agent amount; and the ring-opening etherification is run at a temperature of about −50° to 100° C. for a period of about 7 hours to about 48 hours.

9. The process of claim 8, wherein the base is 2,6-lutidine, pyridine, 2,6-di-t-butylpyridine or triethylamine.

10. The process of claim 5, wherein the base is 2,6-lutidine, pyridine, 2,6-di-t-butylpyridine or triethylamine.

* * * * *

UNITED STATES PATENT AND TRADEMARK OFFICE
CERTIFICATE OF CORRECTION

PATENT NO. : 5,625,078
DATED : April 29, 1997
INVENTOR(S) : Shibano et al

It is certified that error appears in the above-identified patent and that said Letters Patent is hereby corrected as shown below:

Column 27, line 17: delete "2.67-lutidine" and insert --2,6-lutidine--.

Signed and Sealed this

Thirty-first Day of August, 1999

Attest:

Q. TODD DICKINSON

*Attesting Officer*     *Acting Commissioner of Patents and Trademarks*